(12) United States Patent
Rohr et al.

(10) Patent No.: US 11,887,174 B2
(45) Date of Patent: *Jan. 30, 2024

(54) SYSTEMS AND METHODS FOR ANALYZING LOWER BODY MOVEMENT TO RECOMMEND FOOTWEAR

(71) Applicant: Brooks Sports, Inc., Seattle, WA (US)

(72) Inventors: Eric Rohr, Seattle, WA (US); Pete Humphrey, Mill Creek, WA (US); Carson Caprara, Seattle, WA (US); Andre Kriwet, Seattle, WA (US)

(73) Assignee: Brooks Sports, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/313,907

(22) Filed: May 6, 2021

(65) Prior Publication Data

US 2021/0326962 A1 Oct. 21, 2021

Related U.S. Application Data

(63) Continuation of application No. 16/362,150, filed on Mar. 22, 2019, now Pat. No. 11,023,950, which is a
(Continued)

(51) Int. Cl.
*G06Q 30/0601* (2023.01)
*A61B 5/00* (2006.01)
*A61B 5/11* (2006.01)

(52) U.S. Cl.
CPC ....... *G06Q 30/0631* (2013.01); *A61B 5/0077* (2013.01); *A61B 5/112* (2013.01);
(Continued)

(58) Field of Classification Search
CPC ... A61B 5/0077; A61B 5/112; G06Q 30/0631
See application file for complete search history.

(56) References Cited

U.S. PATENT DOCUMENTS

| 2,541,851 A | 2/1951 | Wright |
| 2,546,827 A | 3/1951 | Albert |

(Continued)

FOREIGN PATENT DOCUMENTS

| EP | 2671559 A1 | 12/2013 |
| GB | 2349798 A | 11/2000 |

(Continued)

OTHER PUBLICATIONS

Bio-Mechanics, Proceedings of the American Society of Biomechanics 13th Annual Meeting, University of Vermont, Aug. 23-25, 1989, 19 pages. Exhibit 1054, Case IPR2018-00577.

(Continued)

*Primary Examiner* — Lam S Nguyen
(74) *Attorney, Agent, or Firm* — Perkins Coie LLP

(57) ABSTRACT

Systems and methods for analyzing lower body movement in low stress and loaded states and selecting footwear are disclosed herein. A system configured in accordance with embodiments of the present technology can include, for example, a plurality of markers and/or sensors and a controller. The markers or sensors can be used to detect lower body movement of a human subject, including inward and outward knee motion and tibia rotation. The controller can be configured to record lower body movement of the human subject in an unloaded state and a loaded state. The controller can further be configured to determine a trend corresponding to a change in the lower body movement from the unloaded state to the loaded state. Based on this trend, the system can select footwear characteristics that counteract any trend away from the lower body movement in the unloaded state.

24 Claims, 18 Drawing Sheets

Related U.S. Application Data continuation of application No. 14/806,466, filed on Jul. 22, 2015, now Pat. No. 10,248,985.

(60) Provisional application No. 62/104,651, filed on Jan. 16, 2015.

(52) U.S. Cl.
CPC ........... *A61B 5/1127* (2013.01); *A61B 5/1121* (2013.01); *A61B 5/7275* (2013.01); *A61B 5/743* (2013.01); *A61B 2503/10* (2013.01); *A61B 2503/12* (2013.01)

(56) References Cited

U.S. PATENT DOCUMENTS

| | | | |
|---|---|---|---|
| 3,237,319 | A | 3/1966 | Wade |
| 4,128,950 | A | 12/1978 | Bowerman et al. |
| 4,183,156 | A | 1/1980 | Rudy |
| 4,471,538 | A | 9/1984 | Pomeranz et al. |
| 4,486,964 | A | 12/1984 | Rudy |
| 4,768,295 | A | 9/1988 | Ito |
| 4,808,469 | A | 2/1989 | Hiles |
| 4,887,367 | A | 12/1989 | Mackness et al. |
| 4,918,838 | A | 4/1990 | Chang |
| 5,042,176 | A | 8/1991 | Rudy |
| 5,197,206 | A | 3/1993 | Shorten |
| 5,319,021 | A | 6/1994 | Christy |
| 5,343,639 | A | 9/1994 | Kilgore et al. |
| 5,572,804 | A | 11/1996 | Skaja et al. |
| 5,575,088 | A | 11/1996 | Allen et al. |
| 5,595,004 | A | 1/1997 | Lyden et al. |
| 5,604,998 | A | 2/1997 | Kita |
| 5,639,445 | A | 6/1997 | Curtis et al. |
| 5,685,090 | A | 11/1997 | Tawney et al. |
| 5,686,167 | A | 11/1997 | Rudy |
| 5,718,063 | A | 2/1998 | Yamashita et al. |
| 5,741,568 | A | 4/1998 | Rudy |
| 5,839,209 | A | 11/1998 | Healy et al. |
| 6,050,001 | A | 4/2000 | Ditrtrich |
| 6,158,149 | A | 12/2000 | Rudy |
| 6,701,529 | B1 | 3/2004 | Rhoades et al. |
| 7,188,439 | B2 | 3/2007 | Dibenedetto et al. |
| 7,334,350 | B2 | 2/2008 | Ellis |
| 7,401,419 | B2 | 7/2008 | Lucas et al. |
| 7,490,416 | B2 | 2/2009 | Townsend |
| 7,896,019 | B2 | 3/2011 | Bettin et al. |
| 10,248,985 | B2 | 4/2019 | Rohr et al. |
| 11,023,950 | B2 | 6/2021 | Rohr et al. |
| 2003/0120353 | A1 | 6/2003 | Christensen |
| 2011/0140897 | A1* | 6/2011 | Purks .................. A61B 5/22 73/379.04 |
| 2013/0231590 | A1 | 9/2013 | Corbett et al. |
| 2016/0180440 | A1 | 6/2016 | Dibenedetto et al. |

FOREIGN PATENT DOCUMENTS

| | | |
|---|---|---|
| JP | 7-9105 | 2/1995 |
| JP | H7-9105 | 2/1995 |
| WO | 03022085 A2 | 3/2003 |
| WO | 03055339 A2 | 7/2003 |
| WO | 2014153201 A1 | 9/2014 |

OTHER PUBLICATIONS

Declaration of Dr. Martyn Shorten in Support of Petition for Inter Partes Review of U.S. Pat. No. 7,490,416, executed Feb. 3, 2018, 185 pages. Exhibit 1047, Case IPR2018-00577.
Patent Owner's Demonstrative Exhibits, 32 pages. Exhibit 2013, Case IPR2018-00577.
Runner's Gazette, Nov. 2004, Issue #323, 3 pages. Exhibit 1050, Case IPR2018-00577.
Webster's Third New International Dictionary 2002 by Merriam-Webster Inc., pp. 202 and 357. Exhibit 2001, Case IPR2018-00577.
ASTM International F 1976, "Standard Test Method for Cushioning Properties of Athletic Shoes Using an Impact Test," download Feb. 2018, 4 pages. Exhibit 1049, Case IPR2018-00577.
Beverly, Jonathan. "The Truth About Energy Return in Your Shoes," Runner's World, Oct. 15, 2015, 4 pages. Exhibit 1070, Case IPR2018-00577.
Cambridge Polymer Group, "The Cambridge Polymer Group Silly Putty(TM) 'Egg'". MIT Edgerton Strobe Laboratories. 2008, 2 pages. Exhibit 1065, Case IPR2018-00577.
Derrick, Timothy R. "The Effects of Knee Contact Angle on Impact Forces and Accelerations," Medicine & Science in Sports & Exercise 2004, American College of Sports Medicine; pp. 832-837. Exhibit 1057, Case IPR2018-00577.
Dow Corning Corporation Material Safety Data Sheet, "Dow Corning(R) 3179 Dilatant Compound," Version Jul. 2, 1997, 7 pages. Exhibit 1011, Case IPR2018-00577.
Dow Corning, Product Information Specialty Lubricants, "Dow Corning 3179 Dilatant Compound," Jun. 21, 2013, 2 pages. Exhibit 1052, Case IPR2018-00577.
Dow Corning, Product Information Specialty Lubricants, "Dow Corning(R) 3179 Dilatant Compound," Jun. 21, 2013, 2 pages. Exhibit 1077, Case IPR2018-00577.
Dow Corning, Safety Data Sheet, "Dow Corning(R) 3179 Dilatant Compound," Version 5, Sep. 14, 2017, 20 pages. Exhibit 1064, Case IPR2018-00577.
Dow Corning, Safety Data Sheet, "Dow Corning(R) 3179 Dilatant Compound," Version 5, Sep. 14, 2017, 20 pages. Exhibit 1078, Case IPR2018-00577.
DuPont Media Center, "Dow and DuPont Stockholders Approve Merger," Jul. 20, 2016, 3 pages. Exhibit 1075, Case IPR2018-00577.
Frederick, E. C. "Kinematically mediated effects of sport shoe design: A review," Journal of Sports Sciences, 4:3, 1986, pp. 169-184. Exhibit 1061, Case IPR2018-00577.
Hennig, Ewald M. et al. "In-Shoe Pressure Distribution for Running in Various Types of Footwear," Journal of Applied Biomechanics, 1995, 11, pp. 299-310. Exhibit 1056, Case IPR2018-00577.
Information Disclosure Statement in U.S. Appl. No. 10/981,139 submitted Feb. 9, 2005, 4 pages. Exhibit 1076, Case IPR2018-00577.
International Search Report and Written Opinion dated Mar. 29, 2016, for International Patent Application No. PCT/US2016/012390 filed Jan. 6, 2016, 11 pages.
LinkedIn jobs, "Senior Director—Applied Footwear Research, Nike, Inc.," Job ID 00409848, 2 pages. Exhibit 1069, Case IPR2018-00577.
Martyn R. Shorten Curriculum Vitae, Jan. 2017, 7 pages. Exhibit 1046, Case IPR2018-00577.
Mientjes, Martine I.V. et al. "Contoured cushioning: effects of surface compressibility and curvature on heel pressure distribution," Footwear Science, vol. 3, No. 1, Mar. 2011, pp. 23-32. Exhibit 2010, Case IPR2018-00577.
Molykote website, "About US, 70 years Trusted Smart Lubrication" 2018, 2 pages. Exhibit 1073, Case IPR2018-00577.
Molykote website, "DOWSIL(TM) 3179 Dilatant Compound" 2018, 1 page. Exhibit 1074, Case IPR2018-00577.
Nigg, B. M. et al. "Effect of viscoelastic shoe insoles on vertical impact forces in heel-toe running," The American Journal of Sports Medicine, vol. 16, No. 1, 1988; pp. 70-76. Exhibit 1058, Case IPR2018-00577.
Nigg, B. M. et al. "The Influence of Running Velocity and Midsole Hardness on External Impact Forces in Heel-Toe Running," J. Biomechanics vol. 20, No. 10, pp. 951-959, 1987. Exhibit 1059, Case IPR2018-00577.
Nigg, Benno M. et al. "Influence of Heel Flare and Midsole Construction on Pronation, Supination, and Impact Forces for Heel-Toe Running," International Journal of Sport Biomechanics, 1988, 4, pp. 205-219. Exhibit 1060, Case IPR2018-00577.
Notice of Allowance for U.S. Appl. No. 10/996,235, dated Jul. 14, 2008, 4 pages. Exhibit 1019, Case IPR2018-00577.
Office Action for U.S. Appl. No. 10/996,235, dated Dec. 27, 2007, 13 pages. Exhibit 1015, Case IPR2018-00577.

(56) References Cited

OTHER PUBLICATIONS

Office Action for U.S. Appl. No. 10/996,235, dated Jan. 29, 2008, 11 pages. Exhibit 1017, Case IPR2018-00577.
Office Action for U.S. Appl. No. 10/996,235, dated Sep. 7, 2007, 7 pages. Exhibit 1014, Case IPR2018-00577.
Office Action for U.S. Appl. No. 10/996,235, dated Mar. 5, 2007, 5 pages. Exhibit 1072, Case IPR2018-00577.
Petitioner Brooks Sports, Inc.'s Materials, "Demonstrative Exhibits," revised. May 9, 2019, 153 pages. Exhibit 1081, Case IPR2018-00577.
Response and Amendment to Office Action dated Jan. 29, 2008 for U.S. Appl. No. 10/996,235, received by USPTO on May 29, 2008, 13 pages. Exhibit 1018, Case IPR2018-00577.
Response and Amendment to Office Action dated Sep. 7, 2007 for U.S. Appl. No. 10/996,235, received by USPTO on Jan. 5, 2008, 66 pages. Exhibit 1016, Case IPR2018-00577.
Shorten, M. et al. "The 'heel impact' force peak during running is neither 'heel' nor 'impact' and does not quantify shoe cushioning effects," Footwear Science, vol. 3, No. 1, Mar. 2011, pp. 41-58. Exhibit 1048, Case IPR2018-00577.
Shorten, Martyn et al. "In-Shoe Pressure Distribution: An Alternative Approach to Analysis," Biomechanica LLC, 2 pages. Exhibit 1063, Case IPR2018-00577.
Shorten, Martyn et al. "The Effects of Shoe Cushioning on Impact Force During Running." Nike Sports Research Laboratory. 2 pages. Exhibit 1062, Case IPR2018-00577.
Shorten, Martyn R., "Elastic Energy in Athletic Shoe Cushioning Systems," Abstract. International Society of Biomechanics XII Congress 1989, p. 1082. Exhibit 1055, Case IPR2018-00577.
Shorten, Martyn R., "The Energetics of Running and Running Shoes," J. Biomechanics vol. 26, Suppl. 1, pp. 41-51, 1993. Exhibit 1053, Case IPR2018-00577.
The Dow Chemical Company, "Dow Completes Strategic Ownership Restructuring of Dow Corning Corporation," Jun. 1, 2016, 2 pages. Exhibit 1079, Case IPR2018-00577.
U.S. Patent and Trademark Office Before Patent Trial and Appeal Board, Telephonic Hearing transcript, Sep. 21, 2018, 28 pages. Exhibit 2004, Case IPR2018-00577.
U.S. Patent and Trademark Office Before the Patent Trial and Appeal Board, "Reply Declaration of Dr. Martyn Shorten in Support of Petition for Inter Partes Review of U.S. Pat. No. 7,490,416," Feb. 26, 2019, 79 pages. Exhibit 1071, Case IPR2018-00577.
U.S. Patent and Trademark Office Before the Patent Trial and Appeal Board, Declaration of Gareth H. McKinley, Ph.D, May 16, 2018, 30 pages. Exhibit 2003, Case IPR2018-00577.
U.S. Patent and Trademark Office Before the Patent Trial and Appeal Board, Declaration of Gareth H. McKinley, Ph.D, Nov. 28, 2018, 40 pages. Exhibit 2011, Case IPR2018-00577.
U.S. Patent and Trademark Office Before the Patent Trial and Appeal Board, Deposition of Gareth H. McKinley, Ph.D, Feb. 14, 2019, 220 pages. Exhibit 1068, Case IPR2018-00577.
U.S. Patent and Trademark Office Before the Patent Trial and Appeal Board, Deposition of Martyn R Shorten, Ph.D., Nov. 8, 2018, 156 pages. Exhibit 2009, Case IPR2018-00577.
U.S. Patent and Trademark Office Before the Patent Trial and Appeal Board, Deposition of Martyn R Shorten, Ph.D., vol. II, Mar. 21, 2019, 196 pages. Exhibit 2012, Case IPR2018-00577.
U.S. Appl. No. 60/539,288, filed Jan. 26, 2004, 8 pages. Exhibit 1010, Case IPR2018-00577.
U.S. Appl. No. 60/548,077, filed Feb. 26, 2004, 8 pages. Exhibit 1012, Case IPR2018-00577.
Utility U.S. Appl. No. 10/996,235, filed Nov. 23, 2004, 33 pages. Exhibit 1013, Case IPR2018-00577.
Xu, C. et al. "Anti-impact response of Kevlar sandwich structure with silly putty core," Composites Science and Technology 153 (2017) pp. 168-177. Exhibit 1067, Case IPR2018-00577.

* cited by examiner

Fig. 10

SYSTEMS AND METHODS FOR ANALYZING LOWER BODY MOVEMENT TO RECOMMEND FOOTWEAR

CROSS REFERENCE TO RELATED APPLICATIONS

This application is a continuation of U.S. patent application Ser. No. 16/362,150, filed Mar. 22, 2019, and titled SYSTEMS AND METHODS FOR ANALYZING LOWER BODY MOVEMENT TO RECOMMEND FOOTWEAR, which is a continuation of U.S. patent application Ser. No. 14/806,466, filed Jul. 22, 2015, and titled SYSTEMS AND METHODS FOR ANALYZING LOWER BODY MOVEMENT TO RECOMMEND FOOTWEAR, which claims priority to and the benefit of U.S. Provisional Patent Application No. 62/104,651, filed Jan. 16, 2015, and titled SYSTEMS AND METHODS FOR ANALYZING LOWER BODY MOVEMENT TO RECOMMEND FOOTWEAR, both of which is are incorporated herein by reference in their entirety.

TECHNICAL FIELD

The present technology is related to footwear. In particular, at least some embodiments configured in accordance with the present technology are related to systems and methods for analyzing body movement, and recommending footwear based on the movement analysis.

BACKGROUND

Athletic shoes, in particular running shoes, are typically designed to correct for perceived deficiencies in athletes' gaits and encourage running with a neutral gait. In a neutral gait, which is widely considered the ideal running motion, the foot maintains a balanced transition from heel strike to foot propulsion without placing undue stress on the lower leg, including the ankles and feet. Accordingly, certain running shoes are designed varying degrees of support on the medial side of the shoe to help guide or control mild, moderate, or severe overpronation (i.e., the motion of the foot rolling excessively inward through the foot strike). Similarly, other types of running shoes are designed with varying degrees of support on the lateral side to correct for underpronation or supination (i.e., the motion of the foot rolling outward through the foot strike). Still other running shoes are moderately cushioned for shock absorption to encourage a neutral gait.

Gait analysis is often used to characterize an athlete's running motion (e.g., overpronation, underpronation, or neutral pronation) and select a running shoe based on the athlete's gait. Specialty running stores, for example, typically have trained associates that watch athletes run a short distance (e.g., in the store or on a treadmill) to analyze their gaits, and recommend running shoes based on their assessment. Video systems have also been developed that visually record athletes running on treadmills to capture and review the athlete's movement characteristics or patterns while running. The captured data can be used to identify potential concerns with an athlete's gait. Regardless of the manner in which the athlete's gait is analyzed, the objective when selecting a running shoe is to correct for any lower body movement outside of a neutral gait so that the running shoe allows the athlete to run with a substantially neutral gait.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

FIGS. 10-17 are a series of block diagrams illustrating aspects of a user interface of an application or other computer program associated with a body motion analysis system configured in accordance with an embodiment of the present technology.

DETAILED DESCRIPTION

Systems and methods configured in accordance with at least some embodiments of the present technology analyze an individual's lower body movement and/or other biophysical data in an unloaded or low stress state and in a loaded state. This information can then be used to determine an appropriate shoe for the individual that allows the individual to run or otherwise move in the loaded state in a manner similar to the individual's lower body movement in the unloaded/low stress state. Certain details are set forth in the following description and in FIGS. 1-18 to provide a thorough understanding of various embodiments of the disclosure. One skilled in the art, however, will understand that the present technology may have additional embodiments, and that other embodiments of the technology may be practiced without several of the specific features described below, while still other embodiments of the disclosure may be practiced with additional details and/or features. For example, many of the systems and methods described below refer to analyzing lower body motion for selecting running shoes. However, in other embodiments the systems and methods disclosed herein may be used to select footwear for other activities that benefit from specialized footwear, such as walking or playing certain sports (e.g., tennis, soccer, basketball, football, etc.). Other details describing well-known structures and components often associated with detecting and analyzing body movement, however, are not set forth below to avoid unnecessarily obscuring the description of various embodiments of the disclosure.

As used herein, the term "unloaded state" refers to a condition in which a person's lower body moves substantially without being subject to any load or the associated stress or while only being subject to minimal loads or the associated low level of stress. For example, a human subject (e.g., an athlete, a worker, a patient, etc.) can be said to be in an unloaded state when standing flat footed in an athletic position and performing two-legged vertical squats (i.e., a low stress environment) or when swinging his or her legs back and forth while his or her body is suspended in the air (i.e., a substantially zero stress environment). Conversely, the terms "loaded state" and "active state" refer to conditions in which the person's lower body is subjected to and absorbs substantially larger loads and the associated higher level of stress, such as when the person is running. In addition, the terms "athlete" and "runner" as used herein should be construed broadly to include human subjects in general. Embodiments of Applicant's technology is discussed below with reference to an athlete or athletes, although the technology can be used in connection with other individuals who may not be considered athletes or athletic.

Figure 1:
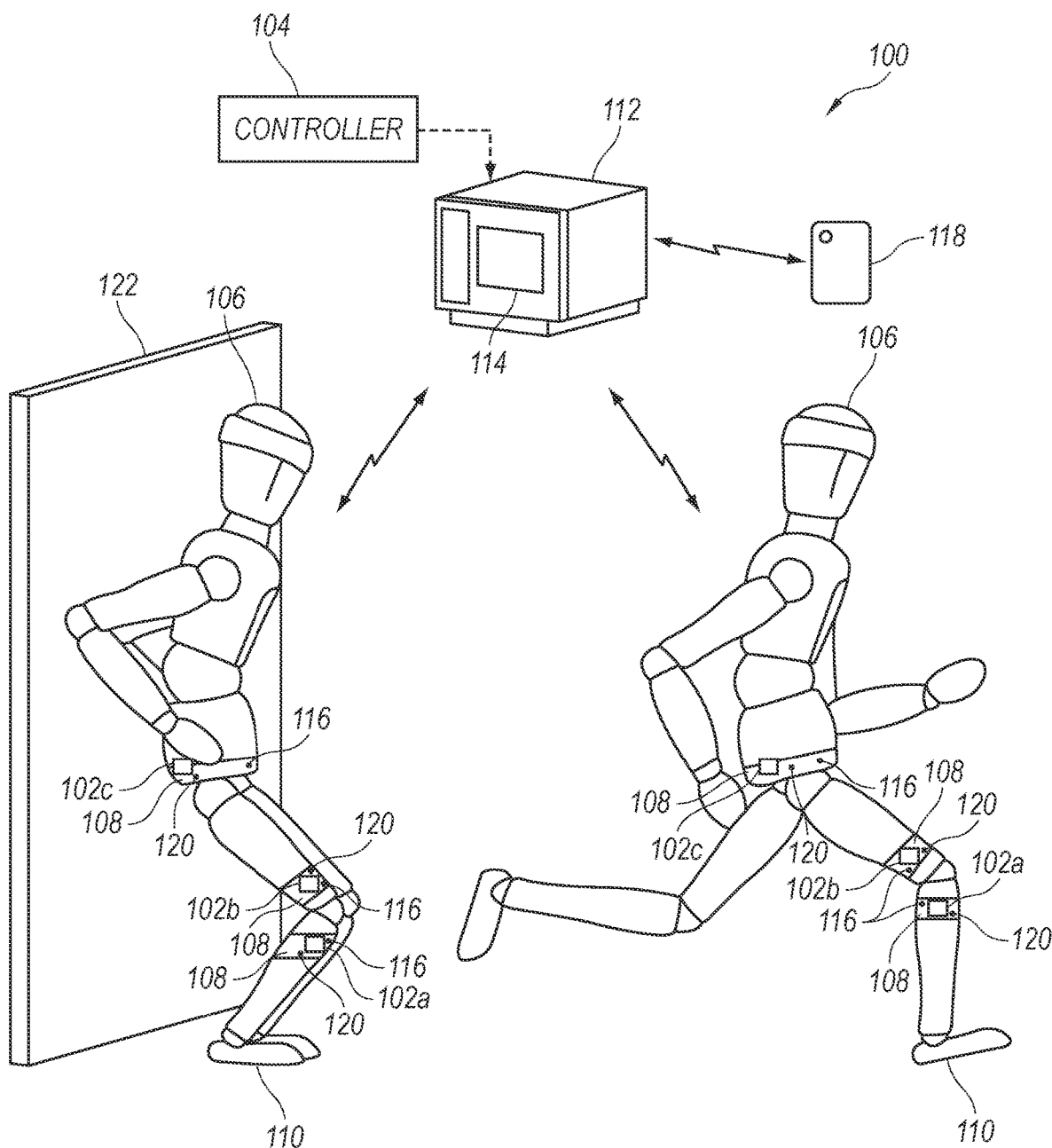
FIG. 1 is a partially schematic view of a system for analyzing lower body movement configured in accordance with an embodiment of the present technology.

FIG. 1 is a partially schematic view of a system 100 for analyzing lower body movement configured in accordance with an embodiment of the present technology. The system 100 includes at least one sensor assembly (identified individually as first through third sensors 102a-102c, respectively, and referred to collectively as "the sensors 102") communicatively coupled to a processor or controller 104 via a wired or wireless connection. The sensors 102 can be attached to various portions of a human subject 106 and configured to detect lower body movement of the athlete 106 in both an unloaded state and a loaded state. In certain embodiments, for example, the sensors 102 can be configured to detect inward and outward (medial and lateral) movement of the athlete's knee and/or internal and external rotation of the lower leg, such as the tibia. In other embodiments, the sensors 102 can be configured to detect other parameters affecting the athlete's body movement, such as head movement, arm movement, and/or relative joint or skeletal movement of the athlete's body. In further embodiments, the sensors 102 and/or other sensing devices of the system 100 can be used to capture other biophysical data, such as forces experienced by portions of the body in the unloaded and loaded states and/or dynamic loading or forces during at least a portion of the range of movement under analysis.

The controller 104 can be configured to record information detected by the sensors 102 and determine trends associated with changes in lower body movement from the unloaded state to the loaded state. For example, the athlete 106 may have a preferred, natural lower body movement in which the athlete 106 moves his or her knees inward or outward and/or rotates his or her tibias inward or outward when moving in an unloaded state, and the knee and/or tibia motion may be exacerbated or reduced when the athlete 106 moves in a loaded state. These trends in the athlete's lower body movement and/or other biophysical data can be used to select footwear or define footwear characteristics that allow the athlete 106 to move in the loaded state in substantially the same manner as he or she would naturally move in the unloaded state. For example, the controller 104 and/or the information provided by the sensors 102 can be used to determine shoe characteristics that counteract trends in lower body movement away from the athlete's natural, unloaded lower body movement. Thus, the system 100 can record data that can be used to select shoes that help athletes keep their lower body movement, forces, and/or other characteristics consistent with the athlete's baseline, unloaded state.

As shown in FIG. 1, the system 100 can include three sensors 102 that can be attached to various portions of the body. In the illustrated embodiment, for example, the first sensor 102a is positioned below the athlete's knee (e.g., near the upper portion of the tibia or calf muscle), the second sensor 102b is positioned above the athlete's knee (e.g., near the lower thigh), and the third sensor 102c is positioned on the torso of the athlete 106 (e.g., on the lower back). The sensor 102 positioned on the lower back (e.g., the third sensor 102c) can serve as a frame of reference for the first and second sensors 102a and 102b. For example, the third sensor 102c can be configured to allow the sensors 102 to self-calibrate and correct for true north to neutralize magnetic field effects, such as when the athlete is moving. In other embodiments, the system 100 can include fewer than three sensors 102, more than three sensors 102, and/or the sensors 102 can be positioned on other portions of the body. For example, the system 100 can be configured to detect the motion of both legs of the athlete 106 and include five sensors 102: one sensor 102 positioned below each knee, one sensor 102 positioned above each knee, and another sensor 102 positioned on the torso. In other embodiments, the system 100 can include additional sensors 102 that detect movement of other portions of the athlete's body (e.g., head movement, arm movement, upper torso movement, etc.) and/or relative joint or skeletal movement of the athlete's body.

The individual sensors 102 can include various different sensing instruments that can detect body motion and orientation. In selected embodiments, each sensor 102 includes three triple axis accelerometers (i.e., tri-modal accelerometers), three triaxial gyroscopes, and three magnetometers. In other embodiments, the individual sensors 102 can include different quantities or types of accelerometers, gyroscopes, and/or magnetometers, and/or include other sensing instruments capable of measuring body movement and/or orientation.

The sensors 102 can be fixed to the body of the athlete 106 so that there is substantially no relative movement with respect to each sensor 102 and the part of the body to which it is attached. As shown in FIG. 1, the sensors 102 can be connected to elastic or expandable bands 108 that extend around various portions of the athlete's body. For example, the band 108 carrying the first sensor 102a can be sized to extend around an athlete's calf, the band 108 carrying the second sensor 102b can be sized to extend around an athlete's thigh, and the band 108 carrying the third sensor 102c can be sized to extend around an athlete's torso. In other embodiments, the band 108 can be sized to extend around other portions of the human body. Each band 108 can include one or more pockets or other features (e.g., clips, snaps, adhesives, etc.) that carry the sensors 102 in substantially fixed positions relative to the band 108. In other embodiments, the sensors 102 can be integrated into the bands 108. In further embodiments, the sensors 102 can be connected to the athlete 106 using other suitable attachment mechanisms. For example, the sensors 102 may include adhesive portions that can temporarily attach the sensors 102 to the athlete's skin or clothing. In still further embodiments, the sensors 102 can be integrated into clothing or athletic gear, such as shirts, pants, undergarments, and/or socks that fit snugly against the athlete's body to avoid or minimize movement of the clothing or gear and associated sensor relative to the selected area of the athlete's body.

The sensors 102 can be configured to measure various parameters associated with the body movement of the athlete 106, such as head movement, arm movement, upper body movement, hip movement, leg movement, knee movement, foot movement, and/or toe movement. In certain embodiments, the sensors 102 measure whether the athlete's knees move medially (inward) or laterally (outward), whether the athlete's tibias rotate internally or externally, and to what degree. In other embodiments, the sensors 102 can be configured to detect other aspects of the athlete's body movement. For example, the sensors 102 can be used and/or configured to detect motion corresponding to foot or toe rotation, upper body movements, and/or other types of body motion that may affect an athlete's gait. In further embodiments, the sensors 102 and/or other sensing devices of the system 100 can be configured to detect other biophysical data. For example, the sensors 102 can be configured to detect static or dynamic forces experienced by portions of the body in the unloaded and loaded states during at least a portion of the range of movement under analysis. In other embodiments, the system 100 can include sensors that detect additional biophysical data that may affect body movement in the loaded and unloaded states, such as heart rate and/or lactic acid levels.

The sensors 102 can measure the various parameters of body movement when the athlete 106 is in an unloaded state, and then again when in a loaded state. For example, to detect lower body movement in the unloaded state, the athlete 106 can be placed in a condition that allows him or her to freely swing his or her legs back and forth about the knee while the sensors 102 record the linear and/or angular movement. This zero- or minimal-stress state may be achieved by suspending the athlete 106 in the air with a harness so that even the gravitational loads from the athlete's body weight are substantially eliminated. Alternatively, the unloaded lower body movement can be detected when the lower body of the athlete 106 is placed under low levels of stress (e.g., substantially only the gravitational loads from the athlete's body weight). For example, the sensors 102 can detect lower body movement as the athlete 106 performs a selected number of smooth, relatively slow, balanced two-legged vertical squats within a predetermined range of motion while standing substantially flat footed (e.g., as illustrated by the athlete 106 on the left side of FIG. 1). In certain embodiments, for example, the sensors 102 detect selected characteristics of the athlete's lower body motion while the athlete 106 performs squats (e.g., 5 or more squats) with a leg/knee range of motion (e.g., knee bend) between about 10°-70°. In other embodiments, the number of squats, the range of motion, and/or the low stress activity may differ. To detect lower body motion in the loaded state, the athlete 106 can run for a predetermined period of time or distance (e.g., 1 minute, 2 minutes, 5 minutes, 1 mile, 2 miles, etc.) while the sensors 102 record the linear and/or angular movement (e.g., as illustrated by the athlete 106 on the right side of FIG. 1). For example, if the athlete is a distance runner, the loaded condition could be similar to the athlete's typical running pace and style or technique used while training. If, on the other hand, the athlete is a short distance runner or sprinter, the loaded condition may be selected as corresponding to a short distance run or sprint at the pace and/or style and technique at which the athlete typically trains. The leg/knee range of motion while running may be about 25°-50°. In other embodiments, the athlete 106 can perform other exercises that subject the lower body to high stresses and/or different ranges of motion while the sensors 102 record various characteristics of loaded lower body movement. The detected information along the same range of leg/knee motion for the unloaded and loaded states can be compared to each other. For example, if the sensors 102 detect data for a range of motion of about 10°-70° in the unloaded state and a range of motion of about 25°-50° in the loaded state, the data detected between 25°-50° and/or a portion thereof (e.g., 35°-40°) may be compared to each other.

In various aspects of the technology, the system 100 can further include neutral footwear 110 that the athlete 106 wears while performing the exercises in the unloaded and/or loaded states. The neutral footwear 110 can be footwear that imparts little to no control or stability to the foot. For example, the neutral footwear 110 may be a cushioned sock, or a sock with an insole (e.g., placed inside of the sock or attached to the bottom of the sock). In other embodiments, the neutral footwear 110 may be a highly neutral, non-cushioned shoe. The neutral footwear 110 does not influence or alter the lower body movement of the athlete 106, or at least only to a minimal degree, and therefore allows the sensors 102 to record the athlete's natural lower body motion in the unloaded and loaded states. In other embodiments, the athlete 106 can perform the low stress and higher stress exercises while barefoot, or while wearing other types of footwear that will still allow the system 100 to determine the athlete's natural lower body motion in the unloaded and loaded states.

As shown in FIG. 1, the controller 104 can be part of a computer 112 or console. The computer 112 can be a server/host computer, a personal computer (e.g., a laptop), a tablet computer, a smart phone, and/or another type of computing device. In the illustrated embodiment, the computer 112 includes a display 114 (e.g., a screen) that can display detected measurements from the sensors 102 and/or information related to the sensed data. For example, the display 114 can be configured to display graphs and/or charts that characterize the athlete's lower body movement, as well as information associated with footwear recommendations based on how the athlete's lower body movement is characterized. In other embodiments, the computer 112 and the display 114 are separate devices. For example, the computer 112 may be a server computer located in a remote facility, and the display 114 may be part of another computing device (e.g., a laptop, tablet, or smart phone) used in a retail establishment, an athletic testing facility, or at a consumer's home and configured to receive signals from the remote computer 112 (e.g., via the Internet or an intranet).

As discussed above, the controller 104 can be operably coupled to the sensors 102 so that it can receive data detected by the sensors 102 and/or send signals to the sensors 102. For example, the controller 104 can execute automated control algorithms to initiate, terminate, and/or adjust operation of one or more of the sensors 102 and/or receive control instructions from a user (e.g., a retail sales associate, a technical expert, and/or a consumer). The controller 104 can further be configured to provide feedback to a user based on the data detected by the sensors 102 via an evaluation/feedback algorithm. For example, the controller 104 can use the sensed data to analyze and/or characterize the athlete's lower body movement in the unloaded and the loaded states, determine or identify changes in the lower body movement in the different states, and/or based upon the body movement data identify footwear characteristics that accommodate or correct for the changes in the lower body movement.

Figure 2:
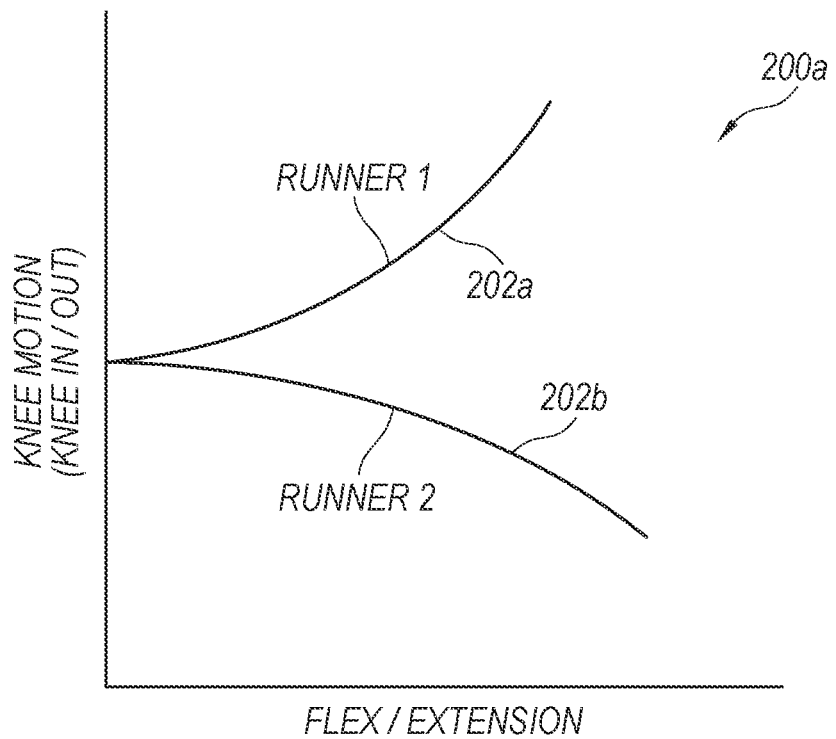
FIG. 2 illustrates a knee motion graph and a tibia rotation graph generated using the system of FIG. 1.
Figure 2:
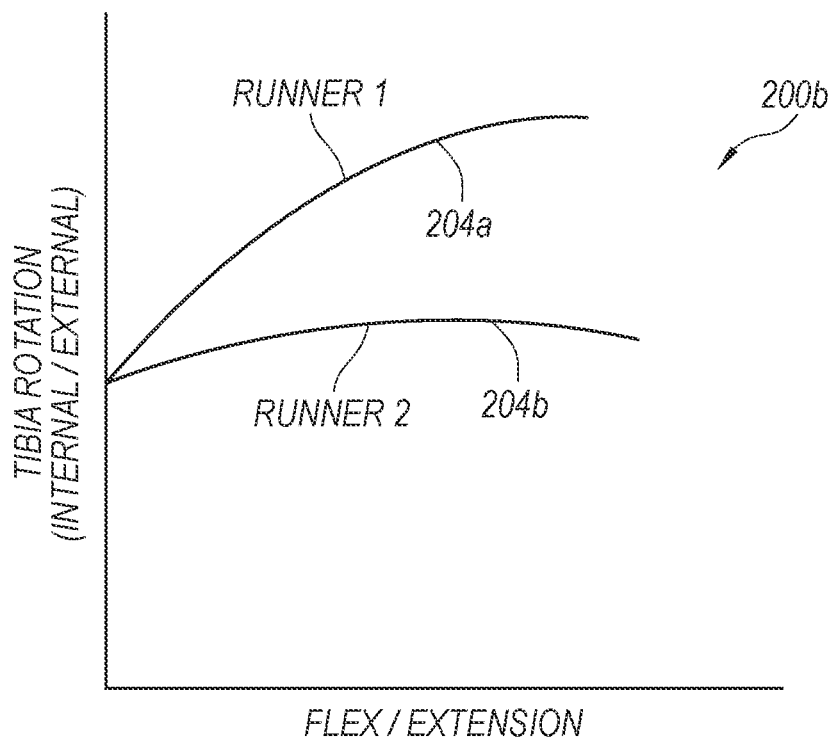

FIG. 2, for example, illustrates graphs (identified individually as a first graph 200a and a second graph 200b, and referred to collectively as "the graphs 200") that may be generated via the controller 104 (FIG. 1) based on the data detected by the sensors 102 (FIG. 1). These graphs 200 may be generated on the computer display 114 (FIG. 1) and/or another display communicatively coupled to the controller 104. As shown in FIG. 2, the first graph 200a plots knee motion (inward/outward) as a function of flexion/extension, and the second graph 200b plots rotation of the tibia as a function of flexion/extension. The graphs 200 can be generated for an individual based on sensed data recorded while he or she moves in an unloaded state to define the individual's baseline lower body movement. The baseline lower body movement corresponds to the way an individual naturally moves his or her lower body without being subject to stress or under low levels of stress (i.e., an individual's preferred pathway or gait). The controller 104 can generate similar knee movement and tibia rotation graphs for the data detected via the sensors 102 while the individual moves in the loaded state. In other embodiments, the controller 104 can be configured to generate additional and/or different graphs representing other characteristics that may affect an individual's lower body movement, such as upper body movement, relative joint or skeletal movement, forces experienced by the athlete's lower body, dynamic loading on the athlete's lower body, and/or biophysical data.

In the illustrated embodiment, the graphs 200 show representative curves of knee motion and tibia rotation for two individuals (Runner 1 and Runner 2) moving in the unloaded state. The first graph 200a indicates that Runner 1 moves his or her knees outward as flexion/extension increases (illustrated by a first curve 202a), whereas Runner 2 moves his or her knees inward as flexion/extension increases (illustrated by a second curve 202b). The second graph 202b shows that Runner 1 tends to rotate his or her tibia inwardly (illustrated by a first curve 204a), and Runner 2 also tends to rotate his or her tibia inwardly, but to a lesser degree than Runner 1 (illustrated by a second curve 204b).

Figure 3:
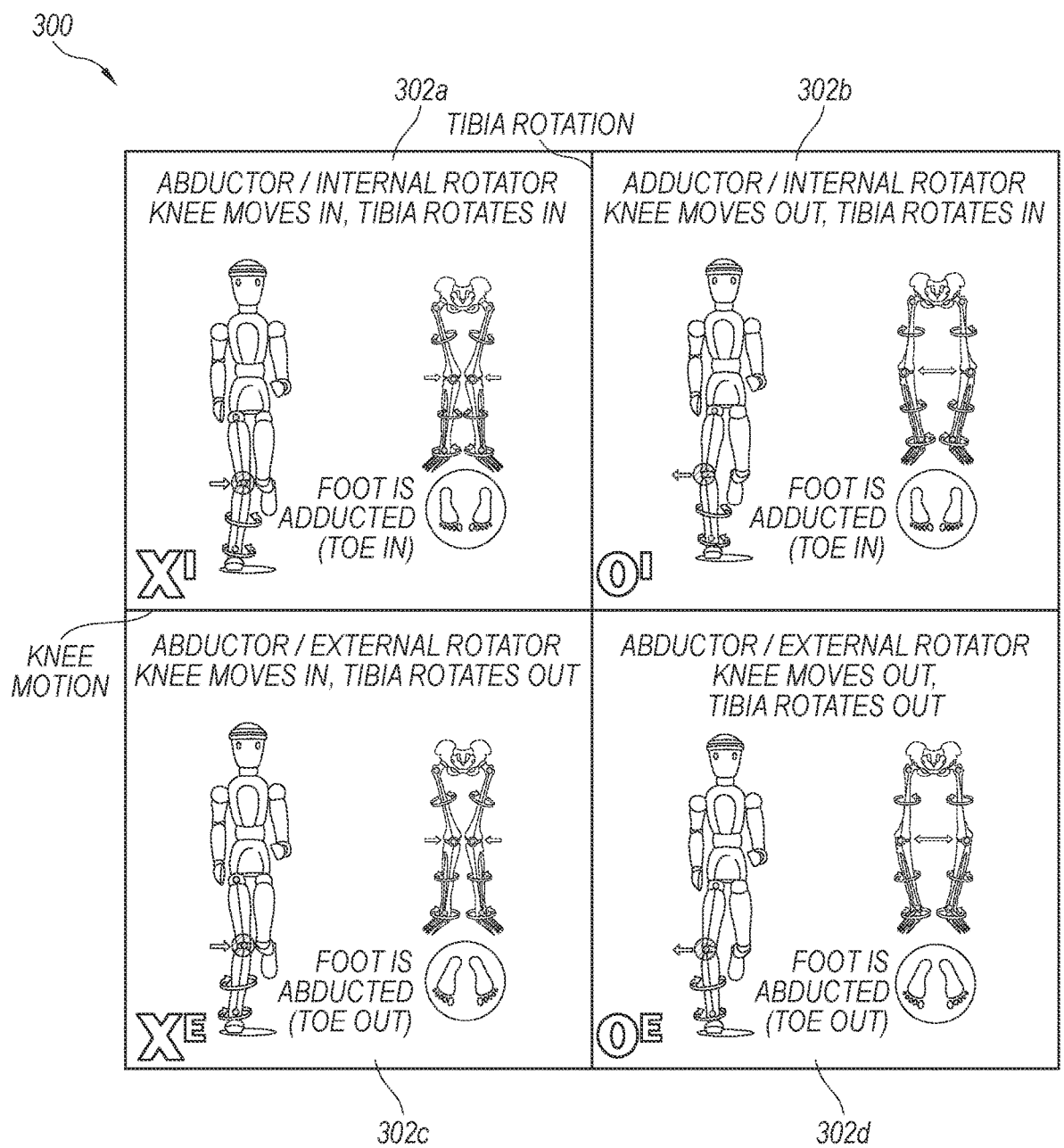
FIG. 3 is a body motion chart configured in accordance with an embodiment of the present technology.

These individualized body motion curves of FIG. 2 can be used to characterize the individual's lower body movement in the unloaded state and/or correlate it to predefined body motion characteristics on a chart or grid. FIG. 3, for example, illustrates such a body motion chart 300 ("chart 300") configured in accordance with an embodiment of the present technology. The chart 300 can be digitally displayed on the computer display 114 of FIG. 1 and/or on another suitable digital display communicatively coupled to the controller 104. In other embodiments, the chart 300 may be a physical chart (e.g., printed on a board or paper).

As shown in FIG. 3, the chart 300 can include four categories, portions, or quadrants (identified individually as first through fourth quadrants 302a-302d, respectively, and referred to collectively as quadrants 302) representing four types of lower body motion that can be determined from sensing knee movement and tibia rotation. For example, in the illustrated embodiment, the x-axis defines the direction and degree of knee motion and the y-axis defines the direction and degree of tibia rotation. Accordingly, the first quadrant 302a represents individuals with inward knee movement and internal tibia rotation (i.e., abductors/internal rotators), the second quadrant 302b represents individuals with outward knee movement and internal tibia rotation (i.e., adductors/internal rotators), the third quadrant 302c represents individuals with inward knee movement and external tibia rotation (i.e., abductors/external rotators), and the fourth quadrant 302d represents individuals with outward knee movement and external tibia rotation (i.e., abductors/external rotators). Using the individualized body motion curves of FIG. 2, the lower body motion of Runner 1 in the unloaded state can be categorized in the second quadrant 302b because Runner 1 has outward knee movement and internal tibia rotation. In contrast, the lower body motion of Runner 2 in the unloaded state falls within the first quadrant 302a because the graphs 200 (FIG. 2) indicate that Runner 2 has inward knee movement and external tibia rotation.

The chart 300 can include additional characteristics of lower body movement that may be directly detected by the sensors 102 (FIG. 1) and/or derived from the sensed data. For example, the chart 300 illustrated in FIG. 3 indicates that internal tibia rotation causes an individual's feet to be adducted (toes directed inwardly toward each other), whereas external tibia rotation causes an individual's feet to be abducted (toes directed outwardly away from each other). This information can be detected directly by sensors positioned on an individual's feet or derived from sensor data taken from other portions of the individual's body (e.g., by detecting tibia rotation using the sensor placement shown in FIG. 1). In other embodiments, the chart 300 can incorporate additional and/or different parameters associated with lower body movements, and/or the chart 300 can be divided into fewer than four or more than four portions associated with different features of lower body movement.

The chart 300 can also include various features that can help a user quickly identify and characterize lower body motion. The chart 300 illustrated in FIG. 3, for example, represents inward (medial) knee motion with the letter "X", outward (lateral) knee motion with the letter "O", internal rotation with the letter "I", and external rotation with the letter "E." Each quadrant 302 of the chart 300 also includes an illustration of a human body moving in the manner associate with that quadrant 302. In other embodiments, the internal/external rotation and inward/outward knee motion can be characterized by different symbols and/or illustrations. In further embodiments, each quadrant 302 of the chart 300 can be a different color to facilitate characterizing each type of body motion.

Figure 4:
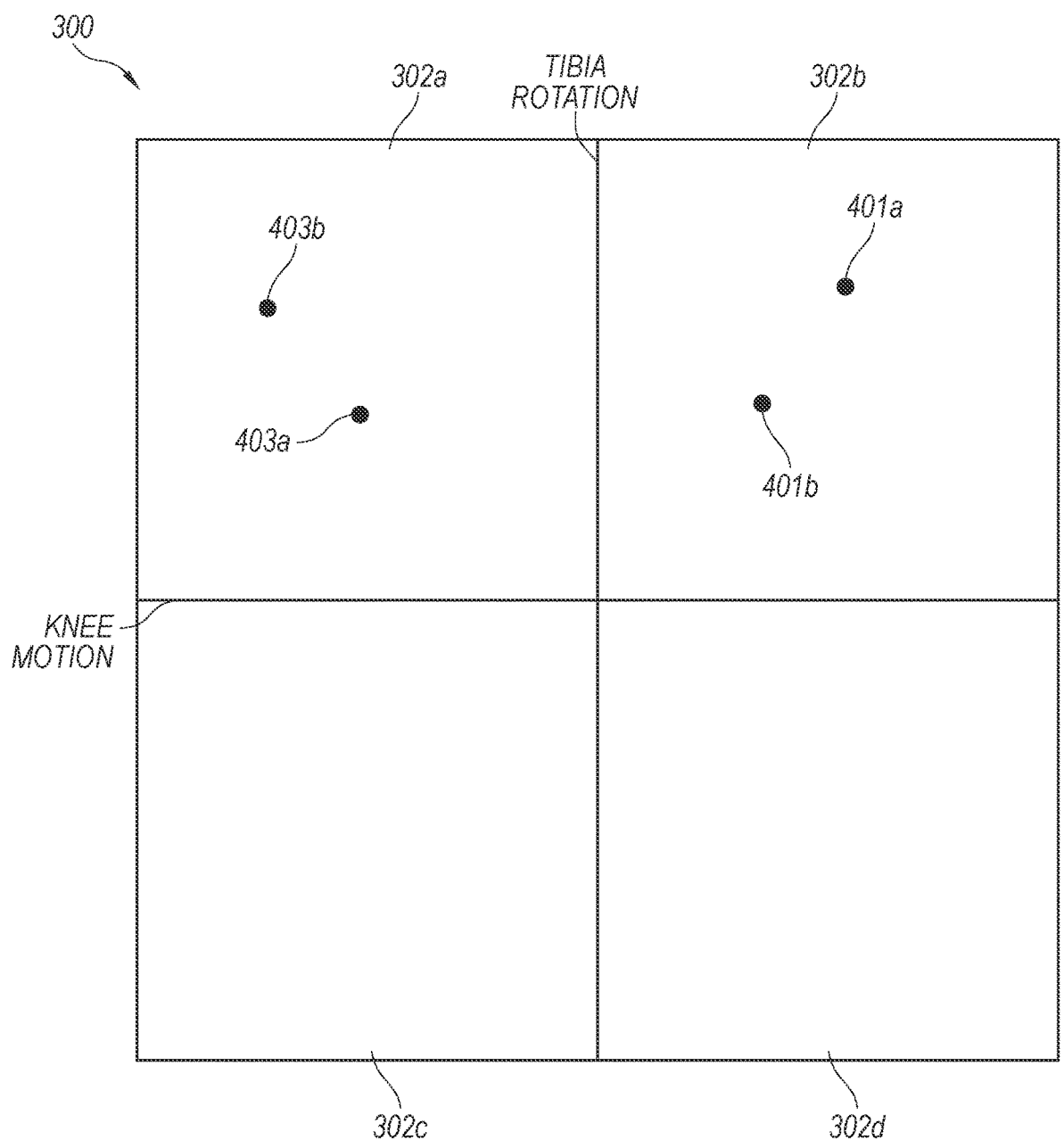
FIG. 4 is a body motion chart illustrating lower body movement of two athletes in an unloaded state and a loaded state in accordance with an embodiment of the present technology.

In certain embodiments, the individualized body motion curves of FIG. 2 and/or other information derived from the sensors 102 (FIG. 1) can be used to determine not only the general category or quadrant 302 associated with an individual's lower body movement, but also identify the individual's specific location within the specific quadrant 302. This information indicates the degree of inward/outward knee motion and internal/external tibia rotation. FIG. 4, for example, illustrates the body motion chart 300 of FIG. 3 (graphics removed for clarity) with the lower body movement of Runners 1 and 2 in the unloaded state plotted as data points 401a and 403a, respectively. In the illustrated embodiment, the data point 401 reflects that Runner 1 has a moderate degree of outward knee motion and a significant degree of internal tibia rotation, and the data point 403 reflects that Runner 1 has a moderate degree of inward knee motion and a mild to moderate degree of internal tibia rotation. The location within the various quadrants 302 of the chart 300 will differ for each individual depending on the individual's degree of knee movement and tibia rotation to reflect his or her baseline lower body movement (i.e., preferred pathway or gait).

In various embodiments, the controller 104 (FIG. 1) can be configured to automatically correlate an individual's lower body movement in the unloaded state with one of the quadrants 302 on the chart 300 (e.g., based on information detected by the sensors 102) and/or determine the individual's specific position within the corresponding quadrant 302. In other embodiments, the controller 104 can provide feedback related to an individual's unloaded, lower body movement to a user (e.g., a third-party evaluator or the athlete himself/herself). For example, the controller 104 can be configured to provide the user with the body motion graphs 200 of FIG. 2 and/or raw data recorded by the sensors 102. The user can then use this information to determine the quadrant 302 associated with the individual's lower body movement in the unloaded state or a location within the particular quadrant 302.

Referring back to FIG. 1, after the athlete's unloaded, lower body movement has been characterized (e.g., on the chart 300 of FIGS. 3 and 4), the system 100 can further be configured to detect, via the sensors 102, characteristics of the athlete's lower body movement in the loaded state (e.g., while running). The data detected while the athlete 106 is in the loaded state can be analyzed in a similar manner as the data gathered from the athlete's lower body movement in the unloaded state. That is, the controller 104, using the data detected by the sensors 102, can plot the athlete's knee motion and tibia rotation in the loaded state as a function of flexion/extension to produce graphs similar to the graphs 200 shown in FIG. 2. This information can then be used to characterize the athlete's loaded, lower body movement on the body motion chart 300 shown in FIGS. 3 and 4. For example, the system 100 can be configured to determine the position on the chart 300 corresponding to the athlete's lower body motion in the loaded state (e.g., a particular quadrant 302 and/or position within a certain quadrant 302). In the chart 300 illustrated in FIG. 4, for example, the loaded, lower body movements of Runners 1 and 2 are represented by data points 401$b$ and 403$b$, respectively.

Lower body movement typically changes when it is subject to stress in the loaded state, and the system 100 can be used to identify such trends. For example, the loaded state may exacerbate any inward/outward knee movement and/or tibia rotation exhibited in the unloaded state. Alternatively, the inward/outward knee movement and/or tibia rotation exhibited in the unloaded state may decrease in the loaded state. These trends in lower body movement can be visualized on a chart or graph by comparing the data points associated with an individual's unloaded lower body movement and the individual's loaded lower body movement. For example, the chart 300 shown in FIG. 4 illustrates data points 401$a$ and 403$a$ corresponding to the lower body movement of Runners 1 and 2 in the unloaded state and data points 401$b$ and 403$b$ corresponding to the lower body movement of Runners 1 and 2 the loaded state. The two data points associated with each runner can be compared to each other to determine the change or trend in that runner's lower body movement from the unloaded to the loaded state. For example, the data point 401$b$ indicates that Runner 1 has outward knee movement and inward tibia rotation in the loaded state, but to a lesser degree than in the unloaded state (indicated by data point 401$a$). The data point 403$b$ indicates that Runner 2 has inward knee movement and inward tibia rotation in the loaded state, but to a greater degree than in the unloaded state (indicated by data point 403$a$). Other individuals will have different changes to their tibia rotation and/or knee movement in response to moving under stress (i.e., in a loaded state), and these trends can be visualized on the chart 300. As discussed above, the detected data for the unloaded and loaded states is compared along the same range of leg/knee motion (e.g., 25°-50°, 30°-45°, 35°-40°, etc.) so that the trends in body movement are identified for the same portion of body movement.

Figure 5:
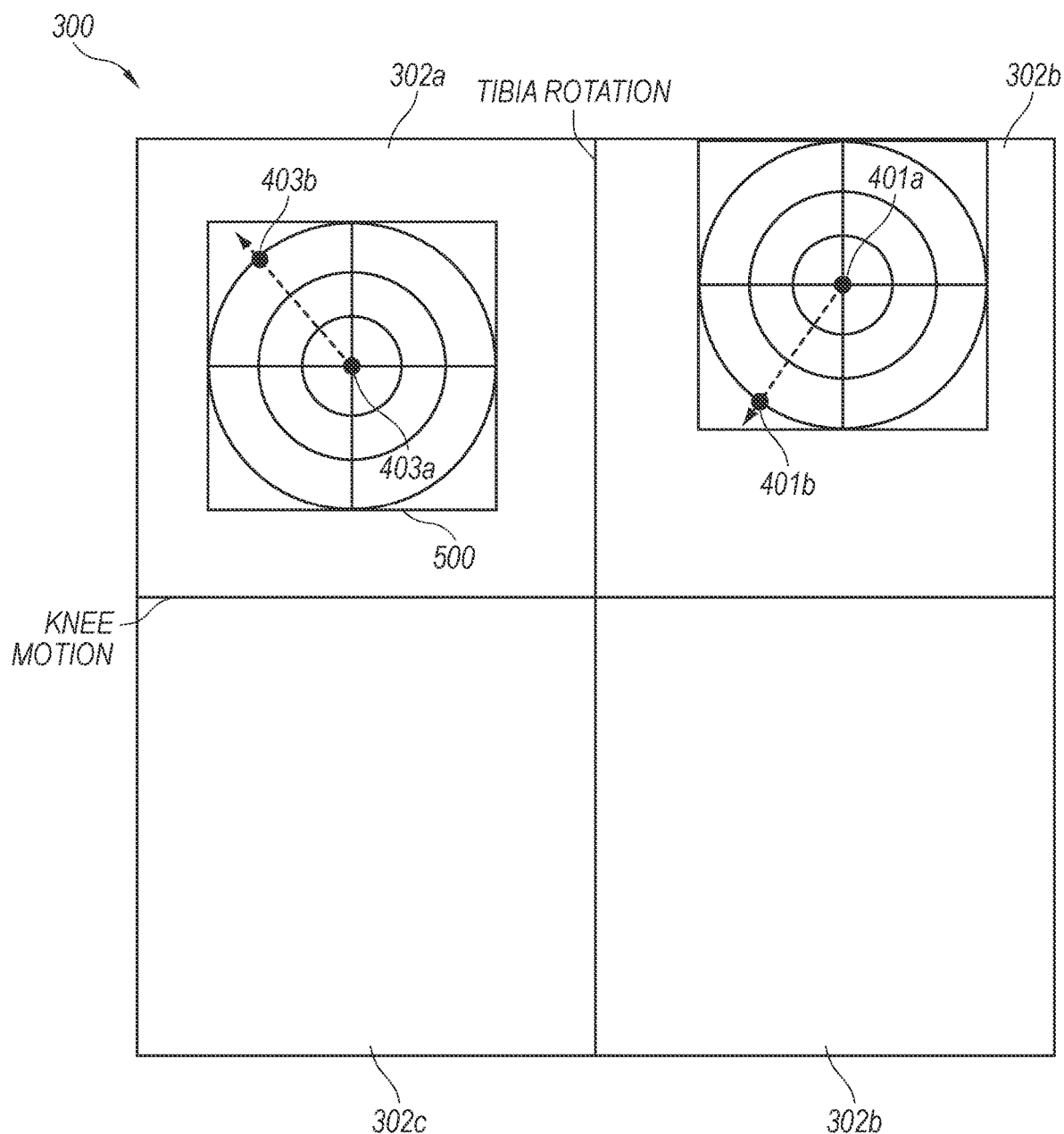
FIG. 5 is the body motion chart of FIG. 4 illustrating trends in the athletes' lower body movement in accordance with an embodiment of the present technology.

In various embodiments, a visual aid may be used to help identify an individual's baseline lower body movement and visualize trends away from the individual's baseline. FIG. 5, for example, shows the body motion chart 300 of FIG. 4 with visual aids 500 configured in accordance with an embodiment of the present technology. In the illustrated embodiment, each visual aid 500 includes a grid with a plurality of concentric rings. The grid can be centered over the data point corresponding to an individual's lower body motion in the unloaded state (e.g., data points 401$a$ and 403$a$) to indicate the individual's baseline or preferred gait.

As shown in FIG. 5, the visual aid 500 can also include a line or vector drawn from the individual's unloaded state data point (e.g., data points 401$a$ and 403$a$) to the individual's loaded state data point (e.g., data points 401$b$ and 403$b$). This allows a user (e.g., a third-party evaluator, an athlete, etc.) to visualize the relative change and trend in lower body movement from the unloaded state (characterized by data point 401$a$/403$a$) to the loaded state (characterized by data point 401$b$/403$b$). In other embodiments, the visual aid 500 may include other graphics or features that facilitate visualization of trends in the changes of lower body movement under a plurality of selected conditions.

The visual aid 500 may be automatically generated on a display via the controller 104 (FIG. 1). For example, the chart 300 may be displayed on a screen (e.g., the display 114 of FIG. 1), and the controller 104 can position the unloaded and loaded state data points for a particular individual in the appropriate places on the chart 300. The controller 104 can then generate the visual aid 500 on the chart 300 centered at the unloaded state data point so as to define a frame of reference corresponding to the individual's baseline lower body motion. Optionally, the controller 104 can generate a line between the unloaded and loaded state data points to further illustrate the trend in lower body movement. In other embodiments, the unloaded and loaded state data points may be manually plotted on the chart 300 and the visual aid 500 may be a physical item, such as a transparent sheet with a graphic printed thereon, that can be superimposed over the chart 300 to help visualize the trend in lower body movement.

Based on an individual's trend of lower body movement from the unloaded to the loaded state, the system 100 (FIG. 1) can be configured to help identify footwear or footwear characteristics that counteract or otherwise reduce trends away from the individual's natural lower body movement in the unloaded state (i.e., an individual's preferred stride or gait) as the individual is actively moving in the loaded state. That is, the data points plotted on the chart 300 (FIG. 5) and the visual aid 500 can illustrate how far away an individual's loaded lower body movement is from his or her preferred, baseline lower body movement, and any change from the individual's baseline can serve as an indicator of the type of shoe characteristics that would allow the individual to remain at or closer to his or her preferred gate (i.e., baseline, unloaded lower body movement).

As an example, the chart 300 illustrated in FIG. 5 indicates that Runner 2 increases inward knee movement and increases internal tibia rotation when in the loaded state. Using this information, the system 100 can provide recommendations of shoes or shoe characteristics that would counteract this additional inward knee movement and internal tibia rotation so that Runner 2's lower body movement in the loaded state is more similar to Runner 2's lower body movement in the unloaded state when he or she runs while wearing the recommended footwear. For example, the shoe recommendations may include additional support or protection to counteract the exacerbated knee and tibia rotation. In contrast, if Runner 2 trended toward less inward knee movement and internal tibia rotation in the loaded state than in the unloaded state, the system 100 could help identify shoes or shoe characteristics that increase inward knee and tibia rotation to help Runner 2 from moving away from and remaining closer to his or her baseline, unloaded lower body movement. In other embodiments, such as when Runner 2's lower body movement does not change much from his or her baseline lower body movement, the system 100 may recommend shoes with more flexibility and be less supportive/protective so as not to impede Runner 2's natural running motion. As further shown in FIG. 5, Runner 1 decreases outward knee movement and decreases internal tibia rotation in the loaded state, and therefore the system 100 can provide recommendations of shoes or shoe characteristics that would reduce the internal knee movement and outward tibia rotation so that Runner 1's lower body movement in the loaded state is more similar to Runner 1's lower body movement in the unloaded state.

Accordingly, the system 100 provides footwear recommendations that aim to allow an individual's lower body to move in the loaded state in the same manner as his or her lower body naturally would in an unloaded state. This differs from the conventional manner of selecting and recommending athletic/running shoes, in which the goal of the shoe recommendation is to modify an individual's gait in the loaded state so he or she has a completely neutral stride (i.e., equivalent to the center of the chart 300 of FIGS. 3-5). This can be done by correcting for any pronation or supination. In contrast, the present system 100 and associated methods can be used to provide shoe recommendations that allow an individual to run or otherwise move in the loaded state in accordance with the individual's baseline, preferred gait for his or her body, even if there is rotational or lateral movement in the individual's unloaded state that does not correspond with a completely neutral stride. It is believed that an individual's lower body movement in the unloaded state generally corresponds to the manner in which the individual's body is naturally built to move. Thus, providing shoe recommendations that bring individuals closer to their natural, unloaded lower body movement (rather than an absolute neutral stride) is expected to enhance performance, comfort, and reduce injury.

In various embodiments, the recommendations provided by the system 100 can be automatically generated. For example, the controller 104 can take into account the sensed data in the loaded and unloaded states, and provide feedback to a user as to what type of shoe or shoe characteristics would best place the athlete into his or her unloaded state. The feedback may be textual, such as recommending stability or control in certain areas. Alternatively or in addition, the recommendations may be conveyed by highlighting the features on a shoe that would allow the athlete to retain his or her unloaded lower body motion, and/or may come in the form of images of particular shoes that are suitable for the individual. In other embodiments, the shoe recommendations and/or footwear characteristics can be displayed directly on the visual aid 500 (FIG. 5). For example, the visual aid 500 can include shoe recommendations or shoe features associated with a trend in a first direction, and may include other shoe recommendations or shoe features associated with a trend in a second direction different from the first direction. In still further embodiments, the recommendations can be provided based on other information gathered from the system 100.

In various aspects of the technology, the system 100 may further be configured to analyze an athlete's lower body movement under specific conditions, and provide footwear recommendations based on the detected data. For example, the system 100 can analyze an athlete's body movements under a load over a greater period of time (e.g., near or at the athlete's fatigue state). The athlete can be instructed to run for a prolonged period of time (e.g., until he or she is at or near a fatigued state) while the sensors 102 detect the athlete's lower body movement. The detected data can be compared to data detected while the athlete was in the unloaded state and/or the initial, loaded state (e.g., under a load for a shorter period of time). The knee movement and/or tibia rotation exhibited by the athlete in the unloaded or initial, loaded state may be significantly exacerbated or otherwise changed when the athlete is in the loaded state for a prolonged period of time. The system 100 (e.g., via the controller 104) can illustrate or identify any trends in the athlete's lower body associated with this prolonged period of exertion, and then recommend footwear or footwear characteristics that counteract trends away from the athlete's lower body movement in the unloaded state. Because the athlete's lower body movement may differ when he or she is in the loaded state for a longer period of time, the footwear that may be suitable for the athlete in the initial, loaded state may have different characteristics (e.g., different types of support or flexibility) than the footwear suitable for the athlete when he or she is subject to a load for a longer period of time.

Similarly, the system 100 can analyze an athlete's lower body movement when the athlete is under a greater load than applied when running (e.g., while sprinting), and provide footwear recommendations suitable for the athlete in these conditions. Thus, the system 100 can recommend different footwear for an athlete depending upon the intended use of the footwear. Accordingly, the system 100 can be used to identify and characterize trends of lower body movement in various different conditions, and define footwear or footwear characteristics that accommodate the type of activity the athlete will perform while wearing the footwear. The system 100, therefore, provides for footwear recommendations that are not only customized to each individual, but to the load conditions in which the individual will use the footwear.

In various embodiments, the system 100 can also be used to design footwear (e.g., running or other athletic shoes) with predetermined characteristics that facilitate or inhibit body movement trends toward or away from the different types of unloaded states characterized on the chart 300 (FIGS. 3-5). For example, unlike conventional running shoes that are predominantly designed to counteract varying degrees of overpronation and underpronation, the system 100 can be used to design footwear (e.g., running shoes) with features that serve one or more of the following functions: lessen internal tibia rotation, lessen tibia rotation, allow for increased internal tibia rotation, allow for increased external tibia rotation, lessen inward knee motion, lessen outward knee motion, allow for increased inward knee motion, and allow for increased outward knee motion. Accordingly, footwear designed via the system 100 can have highly customizable combinations of features that either impede or allow for internal or external tibia rotation and/or inward or outward knee movement and, in certain embodiments, varying degrees of these characteristics. In other embodiments, a specific athlete's lower body movement data can be analyzed to determine the specific footwear characteristics that would allow the athlete to move in the loaded state in a similar manner as he or she does in the unloaded state. This information can then be used to design highly customized footwear for the athlete to best fit his or her needs.

In further embodiments, the system 100 can track an individual's lower body movement over extended periods of time to provide the individual with more feedback as to the individual's lower body movement and trends associated with the lower body movement. For example, an athlete can wear the sensors 102 each time he or she goes on a run or otherwise exercises. In certain embodiments, for example, the sensors 102 may be incorporated into clothing (e.g., undergarments, socks, shorts, etc.) and/or the athletic shoes themselves, or the sensors 102 may be attached to the athlete using other suitable means (e.g., with bands or adhesives). The sensor data recorded during each run can be uploaded to a backend system associated with the system 100 (e.g., the computer 112). This recording can be performed automatically (e.g., in real-time) or manually by the athlete. For example, the sensors 102 can be communicatively coupled to a memory device (e.g., housed in a watch, a flash drive, on a smart phone, in a shoe, etc.), which can temporarily store the sensor data. The stored data can be automatically or manually uploaded to the computer 112.

Once uploaded, the data can be then be analyzed as described above. For example, the data can be used to illustrate the athlete's lower body motion during the run on the body motion graphs 200 of FIG. 2, characterize the athlete's lower body motion (e.g., using the features provided on the chart 300 of FIG. 3), and/or identify the trend of the athlete's lower body movement during the run as compared to the athlete's baseline, unloaded body motion and/or the athlete's loaded body motion recorded during previous runs. This information can be provided to the athlete directly via a user account associated with the system 100. For example, the user account may be accessed via an application on a smart phone, a tablet, and/or computer, or via a website associated with the system 100. The system 100 can further be configured to provide the athlete with personalize footwear recommendations based on the sensed data (e.g., via a website or application). For example, the system 100 can recommend different shoe characteristics or shoe models if the athlete's trend in lower body movement changes and/or recommend new shoes when the trend indicates that the athlete's shoes are no longer performing their intended function (i.e., of allowing the athlete to move in an active state as he or she would in the unloaded state).

Accordingly, this continued tracking of an individual's lower body movement allows the system 100 not only to provide initial recommendations for shoes or shoe characteristics (e.g., while a consumer is in a store), but continue to adjust the data related to an individual's lower body movement to continuously update footwear recommendations for the individual and identify changes in the individual's body movement, potentially before they result in injury. In addition, capturing this data for an extended period of time can be used by shoe manufacturers to better understand body mechanics, how they change over time, and/or how shoes and specific shoe features affect the body mechanics.

In other embodiments, the system 100 can include different or additional features that detect various parameters of an athlete's body movement in the unloaded and loaded states. For example, the sensors 102 can be replaced by a plurality of markers 116 that can be attached to various portions of an athlete, and a video imaging device 118 that can record the movement of the markers 116 in the unloaded and loaded states. The markers 116 can be attached to the athlete in a similar manner as the sensors 102 described above (e.g., using bands, straps, adhesives, integrated into clothing, etc.), and can include features that facilitate recording by the video imaging device 118. For example, the markers 116 may have a high contrast with respect to the rest of the athlete's body, such as white markings. In other embodiments, one or more markers 116 can be attached to portions or ends of shafts that protrude or extend from various portions of the athlete's body to exaggerate the athlete's body movement and make it easier to visualize or otherwise detect via the video imaging device 118. The video imaging device 118 can include a high speed video camera or other video imaging device that is able to capture the movement of athletes in both loaded and unloaded states. In certain embodiments, for example, the video imaging device 118 can be included in a smart phone (e.g., an Apple iPhone), a tablet (e.g., an Apple iPad, a Microsoft Surface, etc.), a personal computer, and/or one or more other personal electronic devices with adequate video resolution. In various embodiments, the system 100 can include both sensors and markers 116 to analyze the athlete's body movement using different modalities.

The video image recorded by the video imaging device 118 can be analyzed via automated computer programs to determine two-dimensional motion data and/or three-dimensional motion data of athletes in the unloaded and unloaded states. For example, the video imaging device 118 can be communicatively coupled to the controller 104 and/or computer 112 via a wired or wireless connection, and the controller 104 or the computer 112 can include a processor that analyzes the raw video data. For example, similar to the sensors 102, the analyzed video data can be used to measure the various parameters of body movement, such as knee, tibia, and/or toe rotation. As shown in FIG. 1, the video imaging device 118 and the computer 112 that analyzes the video data are separate devices. For example, the video imaging device 118 may be a handheld personal electronic device (e.g., a smart phone) that can communicate with a remote central computer associated with the system 110 (e.g., the computer 112) to perform the data analysis. The analyzed data can then be sent back to the user's video imaging device 118 for review and application. In other embodiments, the controller 102 or computer 112 can be integrated with the video imaging device 118 such that the analysis can be performed on the same device that records the data. Unlike other video analysis used today that merely captures and analyzes calcaneus (i.e., heel bone) and/or ankle movement relative to the ground and/or tibia, the video analysis provided by the system 100 provides a user a more comprehensive depiction of body movement and does so in various different states (e.g., unloaded and loaded). In further embodiments, the markers 116 may be omitted and the video image data recorded by the video imaging device 118 can be used alone to analyze body movement.

In further embodiments, the system 100 can include one or more light projecting devices 120 that can be attached to selected portions of the body to illustrate the motion of the selected body portions as the athlete 106 moves in the unloaded and loaded states. For example, the light projecting devices 120 can include lasers and/or other types of light projecting features (e.g., LEDs), and can be attached to the athlete 106 in a similar manner as the sensors 102 described above (e.g., using bands, straps, adhesives, integrated into clothing, etc.).

As shown in FIG. 1, the light projecting devices 120 can be positioned on the athlete 106 to direct identifiable light against a data capture system 122. The data capture system 122 can be a grid and/or another sensing device that detects the light projected onto it from the light projecting devices 120, and thereby captures the movement of the selected portions of the athlete's body in the unloaded and loaded states. For example, the athlete 106 can be positioned forward of the data capture system 122 and move in the loaded and unloaded states while the light projecting devices 120 project onto the data capture system 122, and the data capture system 122 can record the movement of the light. In other embodiments, the data capture system 122 can be defined by a video camera (e.g., the video imaging device 118) that records the light movement. The data capture system 122 can be communicatively coupled to the controller 104 and/or computer 112 via a wired or wireless connection, and the controller 104 or the computer 112 can receive and analyze the data detected by the data capture system 122. For example, similar to the sensors 102, the analyzed data can be used to measure the various parameters of body movement, such as knee, tibia, and/or toe rotation.

Figure 6:
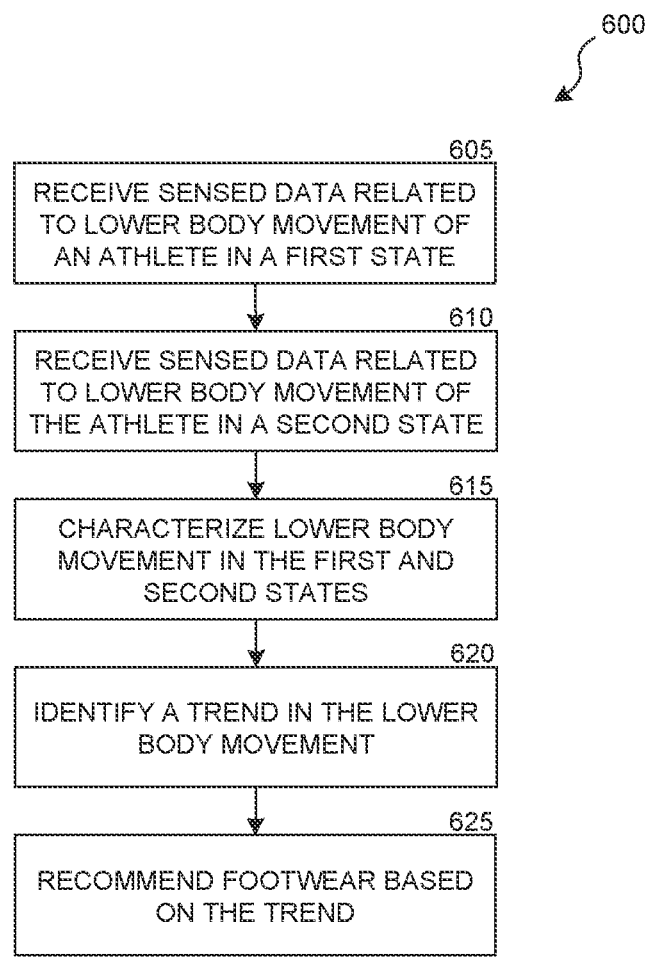
FIG. 6 is a block diagram illustrating a method of selecting footwear for a particular athlete in accordance with an embodiment of the present technology.

FIG. 6 is a block diagram illustrating a method 600 of selecting footwear or footwear characteristics for a particular individual in accordance with an embodiment of the present technology. The method 600 can be implemented using the system 100 of FIG. 1, the body motion graphs 200 of FIG. 2, and/or the chart 300 described above with reference to FIGS. 3-5. For example, the controller 104, the computer 112, the sensors 102, the video imaging device 118, the markers 116, the light projecting devices 120, and/or the data capture system 122 can be used to perform various steps of the method 600, and one or more of the charts 300 or graphs 200 can be generated using the method 600. In other embodiments, the method 600 can be implemented using other suitable systems for evaluating an individual's lower body movements and selecting footwear based on the evaluation. As shown in FIG. 6, the method 600 can include receiving sensed data related to the body movement of an athlete in a first state (block 605). For example, one or more sensors can be attached to the athlete and detect various aspects of the athlete's lower body movement while the athlete moves in the first state. In other embodiments, video imaging and/or light projection devices can be used to detect the athlete's body movement in the first state. This sensed data can then be communicated to a controller or other computing device via a wired or wireless connection. The sensed data can include measurements related to inward and outward knee motion, internal and external tibia rotation, abduction and adduction of the feet, upper body movement, forces experienced by the body, dynamic loading, and/or other aspects associated with body movement. In certain embodiments, the first state is an unloaded state, and the sensors and/or the video imaging device are configured to measure aspects of the athlete's lower body movement (e.g., knee and tibia motion) while the athlete moves in a low stress or zero stress state, such as while the athlete performs a plurality of vertical squats or swings his or her legs back and forth. The sensed data related to the athlete's body motion in the unloaded state is expected to represent the athlete's natural lower body movement (i.e., how the athlete is naturally built to move), and can be used as a baseline to which sensed data from body motion in active, loaded state can be compared. In other embodiments, the first state is a loaded state, and the sensors and/or the video imaging device detect the athlete's lower body movement while the athlete runs or otherwise moves in a high stress state. In this embodiment, the baseline lower body movement can be detected after the lower body movement in the loaded state, or the baseline lower body movement can be previously detected.

The method 600 can continue by receiving sensed data related to body movement of the athlete in a second state different from the first state (block 610). The second state may be a loaded condition, such as running or walking. For example, the method 600 can detect data related to lower body movement while the athlete runs for a predetermined length of time or distance. The predetermined duration or distance may be relatively short (e.g., 30 seconds, 1 minute, 5 minutes, 100 yards, 1 mile, etc.) or may be longer (e.g., 5 miles, 1 hour, etc.) depending upon the type of loaded condition the method 600 aims to measure. For example, if the method 600 is configured to recommend running shoes for a long distance runner, the method 600 can be configured to receive sensed data after the athlete has been running for an extended distance (e.g., 10 miles, 15 miles, etc.). In other embodiments, the second state may be an unloaded or low stress state.

After the sensed data from the first and second states has been received, the method 600 can characterize the athlete's first state of lower body movement and the athlete's second state of lower body movement (block 615). For example, the method 600 can analyze, via a controller, data related to the athlete's body movement in an unloaded state and a loaded state. In certain embodiments, the method 600 can generate one or more graphs related to aspects of the athlete's lower body movement in the unloaded state and the loaded state. For example, the method 600 can plot the athlete's inward/outward knee movement in the unloaded and loaded state on a first graph (e.g., the first graph 200a of FIG. 2), and plot the athlete's internal/external tibia rotation in the unloaded and loaded state on a second graph (e.g., the second graph 200b of FIG. 2). These graphs can define the athlete's stride or gait in the loaded and unloaded states. In other embodiments, the method 600 can plot different or additional parameters of the athlete's lower body movement (detected by or derived from the sensed data) to define the athlete's stride. In certain embodiments, the graphs may be displayed to a user (e.g., the athlete, a third party evaluator, etc.) on a screen (e.g., on a computer, tablet, smart phone, etc.).

The customized graphs can be used to determine where the athlete's loaded and unloaded lower body motion falls within a body motion chart that characterizes predefined types of lower body motion. The body motion chart may be digitally generated or may be a physical chart. The chart may be similar to the chart 300 described above with reference to FIGS. 3-5, and include a plurality of regions (e.g., four quadrants) associated with various aspects of tibia rotation and knee motion. In certain embodiments, the user can view the athlete's body motion graphs and plot the two positions on the chart corresponding to the athlete's body motion in the first and second states (e.g., the unloaded and loaded states). For example, the user can manually position first and second data points corresponding to the athlete's lower body movement in the unloaded and loaded states on the chart. In other embodiments, this step can be performed automatically via feedback algorithms of a controller.

Once the athlete's lower body movement in the first and second states has been defined on the chart, the method 600 can continue by determining a trend corresponding to a change in the athlete's lower body movement from the first to the second state (block 620). The trend can illustrate the manner in which the athlete's lower body movement changes when subject to a load. For example, the trend can show whether the athlete increases or decreases internal or external tibia rotation and/or increases or decreases lateral or medial knee motion, and to what degree. In certain embodiments, the trend can be visually illustrated to the user by drawing a line between the two data points plotted on the chart (corresponding to the athlete's unloaded and loaded lower body motion). In some embodiments, the controller can automatically generate the trend line, and in other embodiments the trend line can be manually inserted by the user. In further embodiments, the method 600 can use additional visual aids (e.g., the visual aid 500 of FIG. 5) to further facilitate visualization of the trend in the athlete's lower body movement.

The athlete's trend in lower body movement from the unloaded to the loaded state can be used to select footwear and/or footwear characteristics for the athlete that reduce or counteract trends away from the athlete's lower body movement in the unloaded state (block 625). For example, the method 600 can identify how the athlete's lower body movement changes in response to moving in the loaded condition (changes in tibia movement and knee motion), as well as the severity of those changes. This information can then be used to identify specific shoe characteristics that mitigate the changes in lower body movement so that the athlete is able to move in the loaded state in substantially the same manner as he or she would naturally move in the unloaded state. In certain embodiments, the method 600 can identify specific shoe models that can provide the desired shoe characteristics. In various embodiments, this portion of the method 600 can be automated. For example, a controller can be configured to analyze the athlete's trend in lower body movement, and automatically provide recommendations related to footwear and/or footwear features. This information can be electronically displayed to the athlete via a display on a computer, tablet, smartphone, and/or other suitable electronic device. In other embodiments, an evaluator can use the information provided by the trend line and/or the body motion chart to provide the athlete with specific footwear recommendations. Accordingly, the method 600 can be used to provide customized footwear recommendations that helps individual athletes maintain their natural, unloaded lower body movement when they move in the loaded state.

Figure 7:
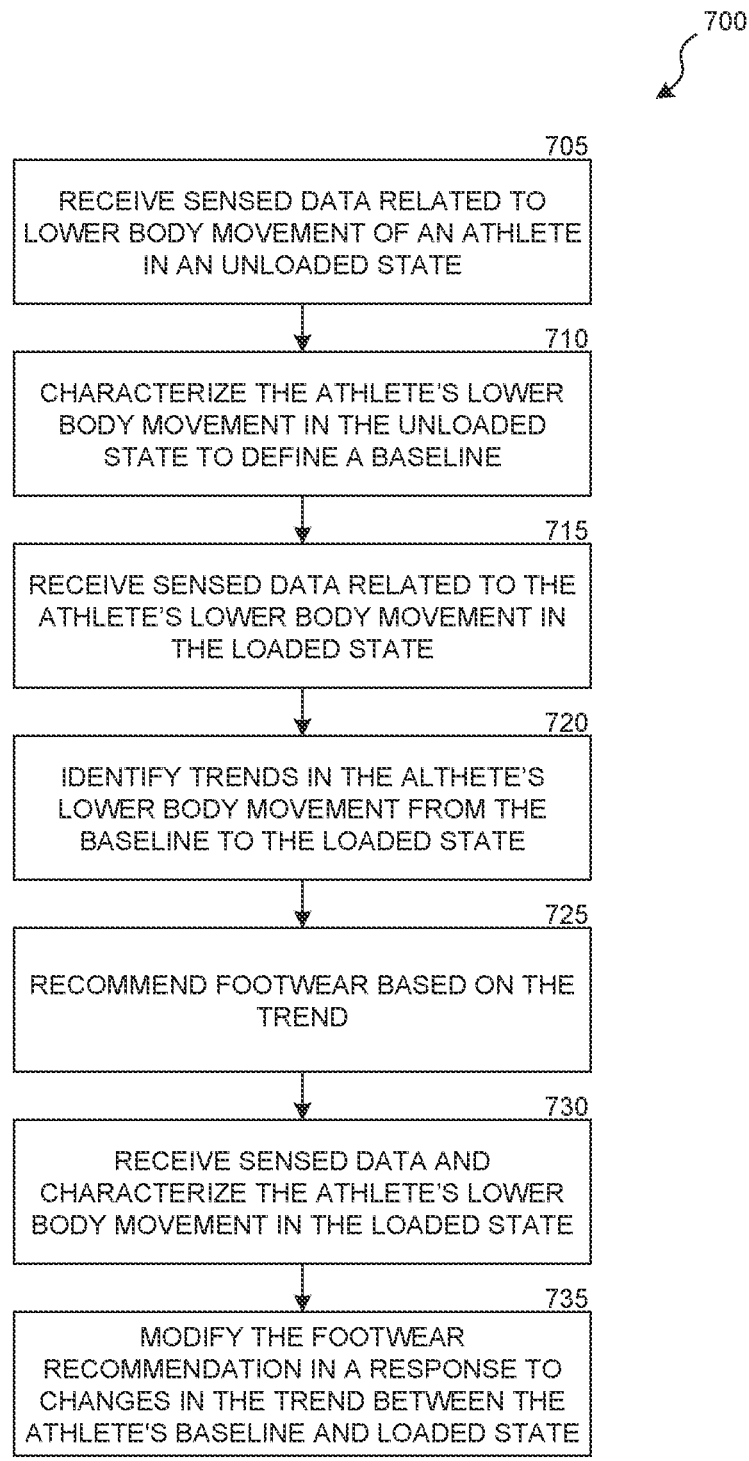
FIG. 7 is a block diagram illustrating a method of monitoring lower body movement in accordance with an embodiment of the present technology.

FIG. 7 is a block diagram illustrating a method 700 of monitoring body motion in accordance with an embodiment of the present technology. The method 700 can be implemented using the system 100, graphs 200, and/or grids or charts 300 described above with reference to FIGS. 1-5, or the method may be implemented using other suitable systems for evaluating body motion and recommending footwear. As shown in FIG. 7, the method 700 can include receiving send data related to an athlete's lower body movement in an unloaded or low stress state (block 705). For example, the sensed data can be recorded on a computer or other storage device communicatively coupled to the sensors and/or a video imaging device. In certain embodiments, the sensed data can be uploaded to a backend computer system (e.g., a server computer) associated with the system for analyzing body movement and recommending footwear. The method 700 can then use the sensed data to characterize the athlete's lower body movement in the unloaded state and define a baseline lower body movement for the athlete (block 710). In certain embodiments, for example, the method 700 can process the sensed data to create graphs associated with one or more detected features of the athlete's lower body movement (e.g., tibia rotation, knee motion, etc.). These graphs can then be used to locate a positon on a grid or chart (e.g., the body motion chart 300 of FIGS. 3-5) that corresponds to the athlete's natural, unloaded lower body motion. This position on the chart can define a baseline that can later be compared to other body movement data. In certain embodiments, the baseline body movement of the athlete can be determined in a retail establishment or testing facility where sensors and/or markers can be attached to the athlete and detect data while the athlete moves in the unloaded state. This detected data (e.g., sensed data or data detected via video imaging systems) can be received by a controller (e.g., at the retail establishing/testing facility or in a remote location) and processed to determine the athlete's baseline body movement. In other embodiments, the athlete can obtain his or her baseline body movement himself or herself using sensors that are communicatively coupled to a backend system, which can in turn process the sensed data and provide the athlete with feedback related to his or her unloaded lower body movement via a website or application. For example, in various embodiments, the sensors may be available for retail purchase, and the athlete can have an account associated with the backend system to view the assessment of his or her baseline, lower body movement.

As shown in FIG. 7, the method 700 can continue by collecting sensed data related to lower body movement when the athlete is in a loaded state (block 715). This information can be detected via sensors and/or video imaging systems while the athlete is in a retail establishment, a testing facility, and/or using the sensors independently. For example, the athlete may place the sensors on his or her body before going on a run, and the sensors can detect various parameters of the athlete's lower body movement during at least a portion of the run. In certain embodiments, the sensors may be incorporated into clothing that the athlete can wear while running. In other embodiments, the sensors can be attached to the athlete with flexible bands and/or adhesive.

The method 700 can continue by characterizing the lower body movement of the athlete in the loaded state in a similar manner as in the unloaded state, and then identifying any trends in lower body movement from the baseline to the loaded, lower body movement (block 720). For example, the method 700 can assess whether the athlete undergoes any changes in tibia rotation, foot rotation, and/or knee motion when being subject to the active, loaded state. As in method 600, this information can be used to provide the athlete with footwear recommendations (e.g., specific shoe models) and/or footwear characteristics (e.g., specific features of shoes) that would adjust the athlete's loaded, lower body movement so that it is more similar to the athlete's unloaded, lower body movement (block 725).

In various embodiments, the method 700 can continue by again recording sensed data related to the athlete's lower body movement in the loaded state, and characterizing the athlete's loaded, lower body movement (block 730), and modify the footwear/footwear characteristic recommendations if the trend between the athlete's baseline and the loaded state has changed (block 735). For example, the method 700 can analyze data detected over the course of several runs. The athlete can wear the sensors during a series of running exercises over a period of time, which may span various different distances and/or different terrain (e.g., hilly terrain, flat terrain, grass, track, pavement, etc.). The additional data captured during the runs may be used by the method 700 to further define the athlete's lower body movement when in the loaded state, which may provide a more accurate characterization of the athlete's loaded, lower body movement. The additional sensed data may also provide feedback as to whether the athlete's trend changes over time and/or when subject to different conditions. For example, if the athlete records his or her lower body movement during multiple runs, his or her gait may change over time (e.g., due to weight loss, strengthen of certain muscles, etc.). The method 700 can identify these changes in trend and update the footwear recommendations for the athlete based on the change in trend. For example, the athlete may have an electronic user account associated with the system that allows the athlete to see his or her trends (e.g., on a chart similar to the chart 300 of FIG. 305) and/or footwear recommendations via a website or application.

Similarly, if the athlete records his or her lower body movement while running on different terrain, the method 700 can provide the athlete with feedback specific to the different types of terrain. For example, the method 700 can characterize the athlete's lower body movement when the athlete runs on hilly terrain, flat terrain, a soft surface (e.g., grass, track, wood chips), and/or a hard surface (e.g., pavement). The athlete's lower body movement may be affected by the type of terrain, and therefore the method 700 can be configured to identify the trend associated with the different types of terrain and provide footwear recommendations for specific types of terrain. For example, the method 700 may be configured to receive input data from the athlete regarding what type of terrain is covered during a particular run. This information can be provided by the athlete and/or other person on a website or application associated with the system, or it may be automatically detected via sensors (e.g., GPS sensors) and uploaded to the system. The method 700 can then provide the athlete with footwear recommendations for specific types of terrain if the athlete's stride is affected differently by certain terrains.

In addition, the method 700 can be used to determine whether the athlete's shoes are helping the athlete to run in a manner more similar to the athlete's baseline body movement. For example, the method 700 can initially recommend footwear or footwear characteristics that facilitate running as the athlete would in the athlete's baseline, unloaded state. Then, the method 700 can detect the athlete's lower body movement during subsequent runs using the recommended footwear. If the data recorded during the subsequent runs does not reduce the trend away from the athlete's unloaded state, or does not reduce it to a desired degree, the method 700 can modify the footwear recommendation to further facilitate the goal of helping the athlete run in a manner equivalent to the athlete's unloaded state.

The feedback provided to the athlete can also or alternatively be provided to shoe manufacturers or retail establishments. This information can be used to design footwear to accommodate various different needs of athletes, as well as indicate when a particular athlete may need to change his or her footwear to counteract or reduce a trend away from the athlete's baseline, unloaded state.

Accordingly, the method 700 can provide athletes, manufacturers, and/or retailers with feedback regarding the athletes' lower body movement in substantially real time (e.g., after each run) and over the course of time and in substantially real time. This information can be used to better identify the needs of the athletes and provide personalized footwear recommendations to individual athletes in real time (e.g., after each run), without waiting until the athlete decides to purchase a new pair of shoes.

Figure 8:
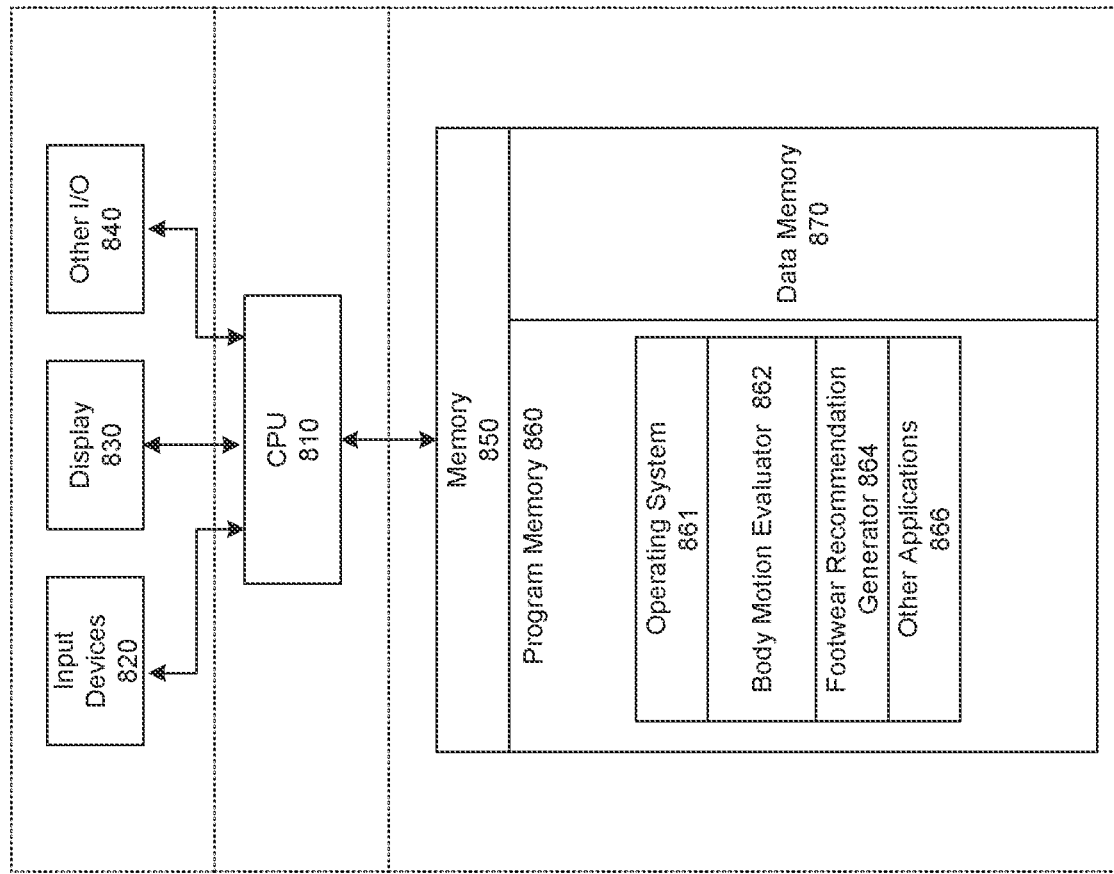
FIG. 8 is a is a block diagram illustrating an overview of devices on which some embodiments of the disclosed technology may operate.

FIG. 8 is a block diagram illustrating an overview of devices 800 on which some embodiments of the disclosed technology may operate. The devices may comprise hardware components of a device 800 for analyzing an athlete's lower body movement and providing footwear recommendations. Device 800 includes one or more input devices 820 that provide input to a CPU (processor) 810, notifying it of actions performed by a user. The actions are typically mediated by a hardware controller that interprets the signals received from the input device and communicates the information to the CPU 810 using a communication protocol. Input devices 820 include, for example, a mouse, keyboard, a touchscreen, an infrared sensor, other sensors, a touchpad, wearable input devices, a camera- or image-based input device, microphone, or other user input devices.

CPU 810 may be a single processing unit or multiple processing units in a device or distributed across multiple devices. CPU 810 may be coupled to other hardware devices, for example, with the use of a BUS, such as a PCI BUS or SCSI BUS. The CPU 810 may communicate with a hardware controller for devices, such as for a display 830. Display 830 may be used to display text and graphics. In some examples, display 830 provides graphical and textual visual feedback to a user. In some implementations, the display includes the input device as part of the display, such as when the input device is a touchscreen or is equipped with an eye direction monitoring system. In some implementations, the display is separate from the input device. Examples of display devices are: an LCD display screen, an LED display screen, a projected display (such as a heads-up display device or a head-mounted device), and so on. Other I/O devices 840 may also be coupled to the processor, such as a network card, video card, audio card, USB, firewire or other external devices, a camera, a printer, speakers, sensors, a CD-ROM drive, a DVD drive, disk drives, or Blu-Ray devices.

The CPU 810 has access to a memory 850. A memory includes one or more of various hardware devices for volatile and non-volatile storage, and may include both read-only and writable memory. For example, a memory may comprise random access memory (RAM), read-only memory (ROM), writable non-volatile memory, such as flash memory, hard drives, floppy disks, CDs, DVDs, magnetic storage devices, tape drives, device buffers, and so forth. A memory is not a propagating electrical signal divorced from underlying hardware, and is thus non-transitory. The memory 850 includes program memory 860 that contains programs and software, such as an operating system 861, a body motion evaluator 862, a footwear recommendation generator 864, and any other application programs 866. The memory 850 also includes data memory 870 that includes any configuration data, settings, user options and preferences that may be needed by the program memory 860, or any element of the device 800.

In some implementations, the device 800 also includes a communication device capable of communicating wirelessly or wire-based with a network node. The communication device may communicate with another device or a server through a network using, for example, TCP/IP protocols. For example, device 800 may utilize the communication device to distribute operations across multiple network devices.

The disclosed technology is operational with numerous other general purpose or special purpose computing system environments or configurations. Examples of well-known computing systems, environments, and/or configurations that may be suitable for use with the technology include, but are not limited to, personal computers, server computers, handheld or laptop devices, cellular telephones, wearable electronics, tablet devices, multiprocessor systems, microprocessor-based systems, set-top boxes, programmable consumer electronics, network PCs, minicomputers, mainframe computers, distributed computing environments that include any of the above systems or devices, and the like.

Figure 9:
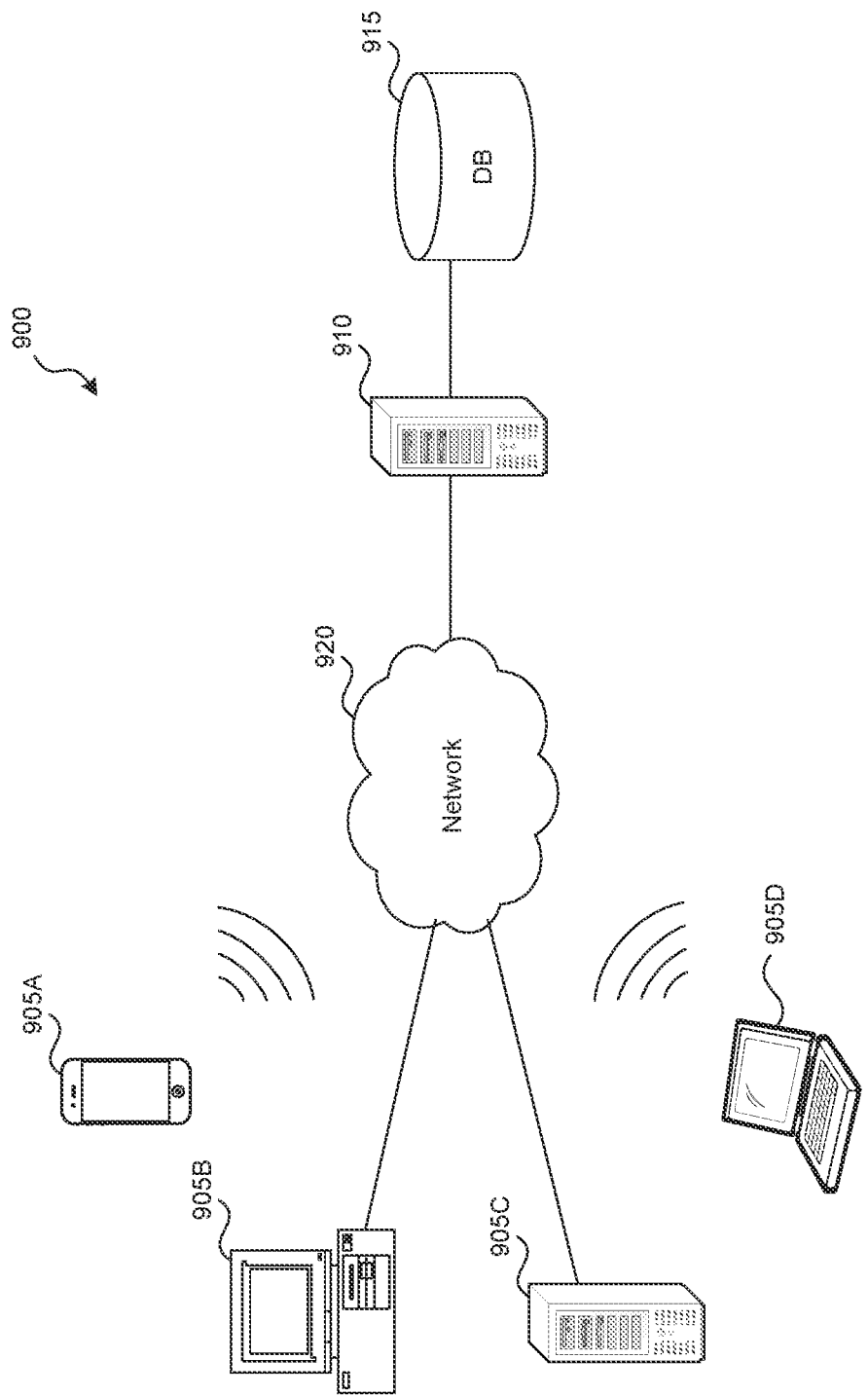
FIG. 9 is a block diagram illustrating an overview of an environment in which some embodiments of the disclosed technology may operate.

FIG. 9 is a block diagram 900 illustrating an overview of an environment in which some embodiments of the disclosed technology may operate. An environment for implementing the technology may include one or more client computing devices 905A-D, examples of which may include device 800 (FIG. 8). Client computing devices 905 may operate in a networked environment using logical connections to one or more remote computers such as server computing device 910 through network 920. Though server computing device 910 and is displayed logically as a single server, server computing device 910 may be a distributed computing environment encompassing multiple machines located the same or at geographically dispirit physical locations. Client computing devices 905 and server computing device 910 may each act as a server or client to other server/client devices. Server 910 may connect to a database 915. Database 915 may warehouse information such as rule cost and probability information from real world observations, benchmarking, or calculations such as the size of a data set corresponding to a particular rule. Though server computing device 910 and database 915 are displayed logically as a single machine, server computing device 910 and database 915 may each be a distributed computing environment encompassing multiple machines located at the same or at geographically dispirit physical locations.

Network 920 can be a local area network (LAN) or a wide area network (WAN), but may also be other wired or wireless networks. The client computing devices 905 can be connected to network 920 through a network interface, such as by wired or wireless communication.

FIGS. 10-17 are a series of display pages or block diagrams (first through eighth block diagrams 1000a-h, respectively; referred to collectively as "block diagrams 1000") illustrating aspects of a user interface of an application or other computer program associated with a body motion analysis system configured in accordance with an embodiment of the present technology. The body motion analysis system can be similar to the system 100 described with reference to FIGS. 1-9 above. In the illustrated embodiment, the user interface of the application is shown on a tablet, and a video camera integrated with the tablet is used to record the runner moving in an unloaded state and a loaded state. The recorded information is then used by the application and/or an associated program (e.g., a program on a server computing device communicatively coupled to the tablet via a network) to analyze the runner's body motion in the unloaded and loaded states. In other embodiments, the application can be accessed with other computing devices, such as smartphones, personal computers, automated kiosks, and/or other suitable devices for interfacing with applications and computer programs. In further embodiments, the computing device running the application is communicatively coupled to a video camera separate from the device, and the information recorded via the camera is received by the application via a wired or wireless connection (e.g., similar to the video imaging device 118 described above with respect to FIG. 1). In additional embodiments, the application can include additional or different block diagrams than those shown in FIGS. 10-17, some of the block diagrams 1000 may be omitted, and/or the block diagrams 1000 may have a different sequential order than shown in FIG. 10-17.

Figure 10:
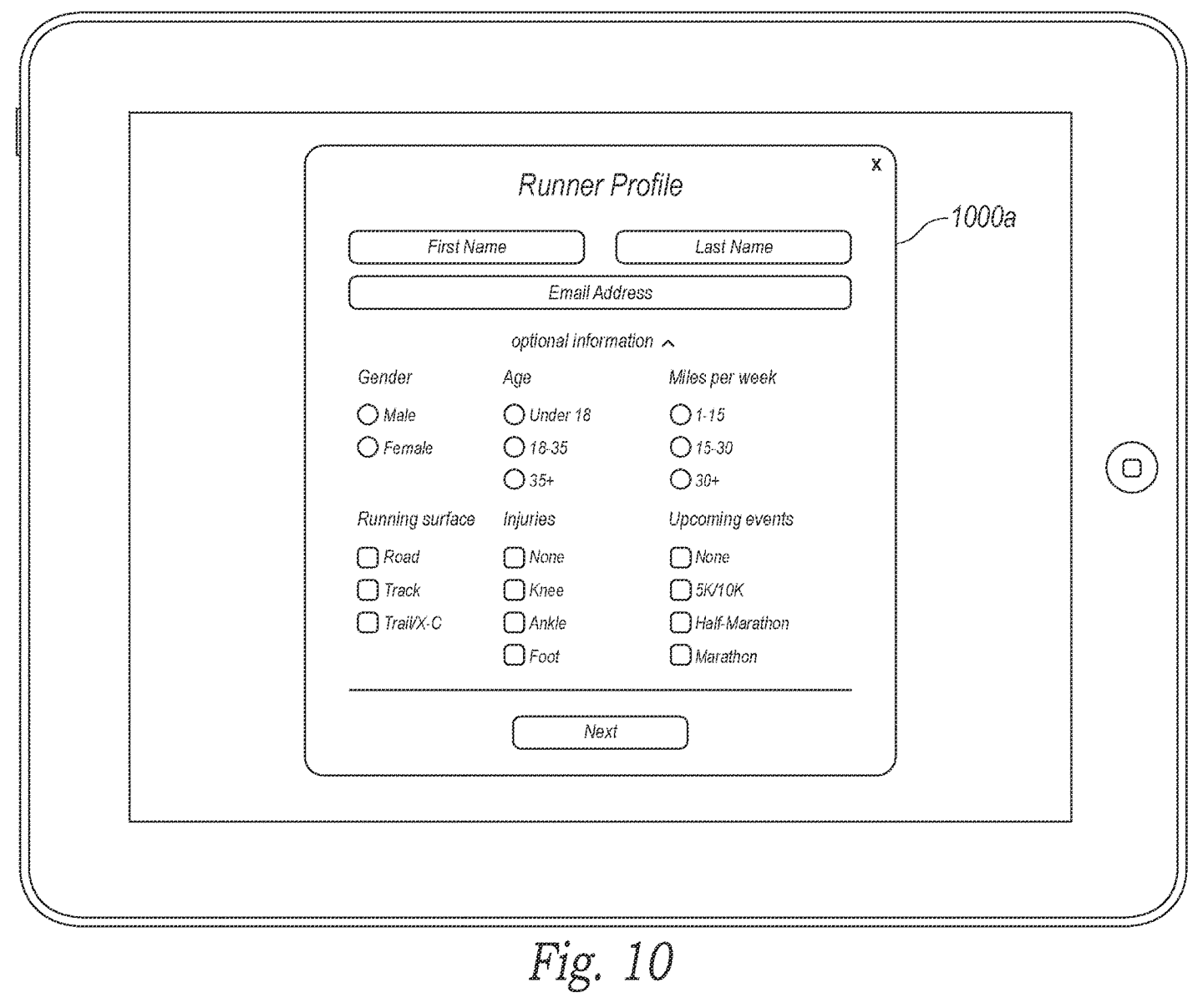

As shown in FIG. 10, the first block diagram 1000a, allows a user (e.g., a retailer, trainer, runner, researcher, etc.) to provide the application with information related to the runner undergoing the body motion analysis. In the illustrated embodiment, for example, the application receives runner identification information and/or running profile, such as the runner's name, email address, gender, age, miles per week, typical or preferred running surface, injuries, and upcoming events. The application can also be configured to receive additional and/or different information, such as the runner's weight, height, running shoe characteristic preferences, and/or other parameters that may affect the body motion analysis and/or a shoe selection based on the body motion analysis. In certain embodiments, the application can be used to create a user account associated with the received email address and/or runner information. The results of the body motion analysis can then be associated with the user account and stored on a database (e.g., the database 915 of FIG. 9) and accessed at a later time by the runner and/or other users (e.g., retailers, shoe manufacturers, trainers, race coordinators, researchers, etc.).

Figure 11:
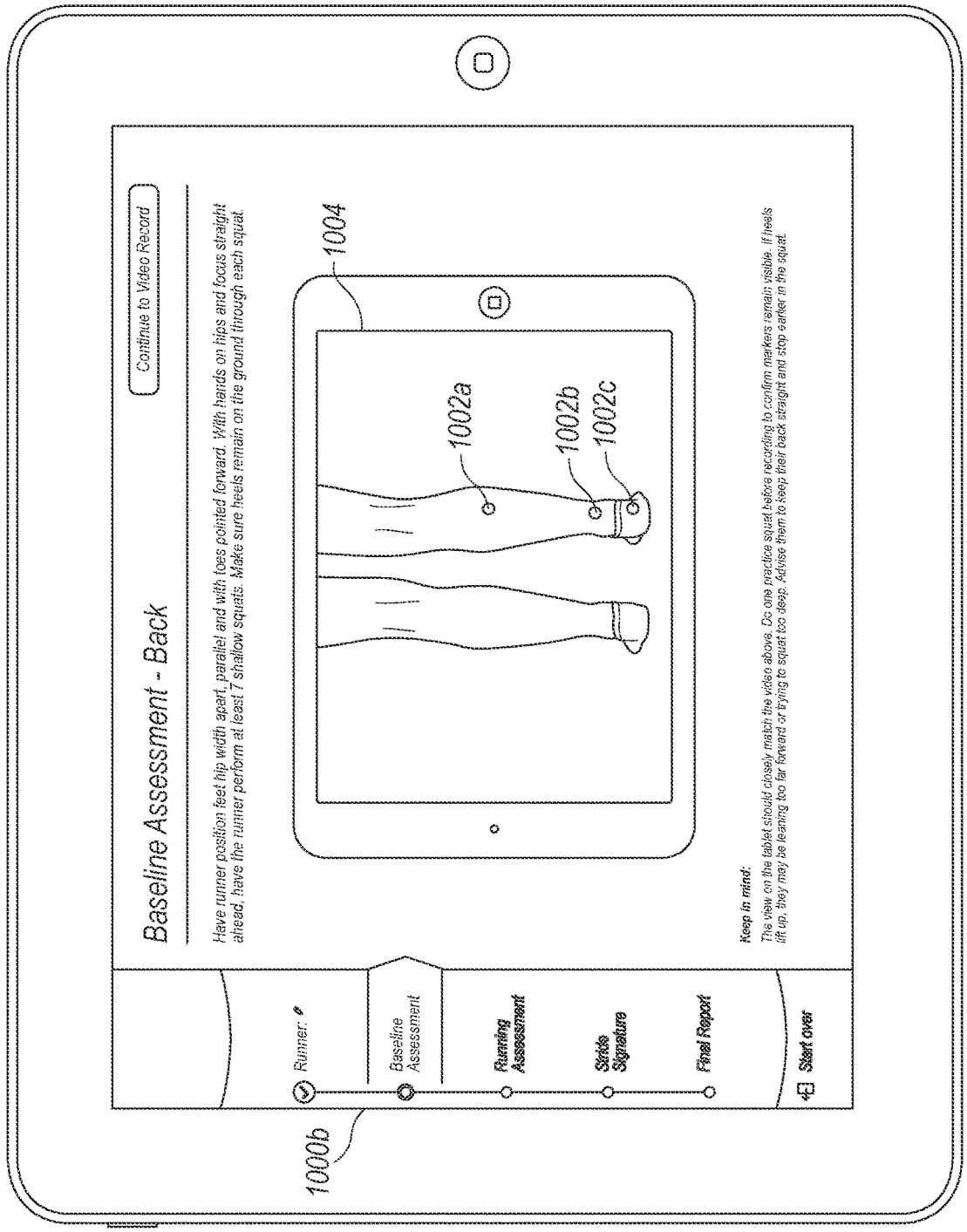
Figure 12:
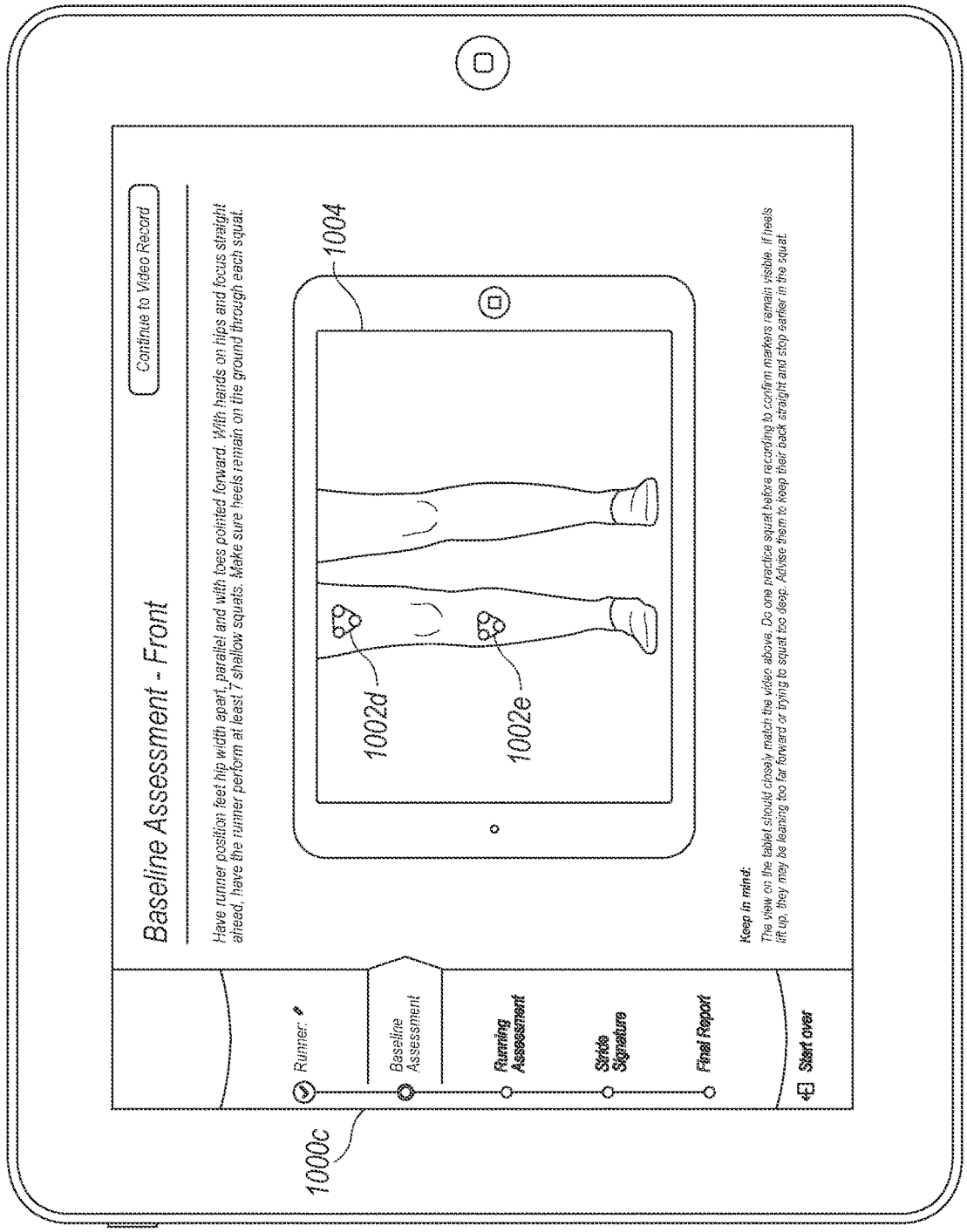

Once the application has received the runner's information, the application continues to the second block diagram 1000b (FIG. 11) and third block diagram 1000c (FIG. 12) to perform a baseline assessment of the runner's body movement. As discussed above, the baseline assessment is performed by recording the runner (via a video camera) as he or she moves in an unloaded state. As shown in FIG. 11, the baseline assessment can begin by recording the runner from the back as the runner performs the unloaded state exercise (e.g., squats), and continue by recording the runner from the front as the runner performs the unloaded state exercise for a second time (FIG. 12). In other embodiments, the order can be reversed such that movement is recorded from the front and then the back. In certain embodiments, two or more cameras can be used to capture the runner's unloaded state movement simultaneously from both the front and the back.

As shown in FIGS. 11 and 12, the second and third block diagrams 1000b and 1000c can provide instructions for performing the baseline assessment, including instructions related to how the runner should move in the unloaded state and how the camera should be positioned in relation to the runner as the runner performs the unloaded state movement. For example, in the embodiment illustrated in FIGS. 11 and 12 the block diagrams 1000b-c provide specific instructions related to the type of unloaded movement (e.g., squats), the number of squats (e.g., at least 7 squats), and other guidance regarding the type of exercise. The block diagrams 1000b, 1000c can also include an image or video 1004 that visually illustrates an example of the unloaded state movement (e.g., a person performing squats in the desired manner) and/or visually indicates the view the camera should have when recorded the runner performing the unloaded movement to facilitate positioning of the camera. For example, in FIG. 11 the video 1004 indicates that the camera should be positioned behind the runner and directed at the back of the runner's legs, and in FIG. 12 the video 1004 indicates that the camera should be positioned in front of the runner and directed toward the font of the runner's legs. When the camera is connected to the device running the application (e.g., when using a tablet), the user can manually hold the camera in the appropriate position for recording runner movement, or a stand may be set up to appropriately position the device. In various embodiments, the stand may be adjustable to accommodate runners of differing heights. In other embodiments, one or more cameras separate from the computing device are positioned in locations appropriate for recording the runner's body movement in the unloaded state.

As further shown in FIGS. 11 and 12, a plurality of markers (identified individually as first through fifth markers 1002a-e, respectively, referred to collectively as "markers 1002") are positioned on the back side and front side of at least one of the runner's legs before the body motion assessment and analysis begins. As shown in FIG. 11, the first marker 1002a is positioned below the runner's knee on the runner's calf, the second marker 1002b is positioned proximate to the runner's achilles tendon, and the third marker 1002c is positioned at or proximate to the back of the runner's heel. As shown in FIG. 12, the fourth marker 1000d is positioned above the runner's knee on the runner's thigh, and the fifth marker 1000e is positioned below the runner's knee on the runner's shin.

Similar to the markers 116 described above with respect to FIG. 1, the markers 1002 can be attached to the runner using adhesives, bands, straps, and/or other suitable attachment means, and can include features that facilitate recording by the camera. For example, the markers 1002 may have a high contrast with respect to the rest of the athlete's body, such as white or brightly-colored markers. In other embodiments, one or more markers 1002 can be attached to portions or ends of shafts that protrude or extend from various portions of the athlete's body to exaggerate the athlete's body movement and make it easier to visualize or otherwise detect via the video camera. In the illustrated embodiment, the first through third markers 1002a-c (FIG. 11) on the back of the runner's same leg each include singular marker elements, whereas the fourth and fifth markers 1002d and 1002e (FIG. 12) on the front of the runner's leg each include three marker elements spaced apart from each other (e.g., in a triangular configuration). The combination of three marker elements (either as separate markers or combined in a single marker) allows a monitoring system of the application or associated program to determine the location of the markers in three-dimensional space relative to each other. In the arrangement of markers shown in FIGS. 11 and 12, this allows the monitoring system to measure tibia rotation and knee movement inward and outward, and this information can be used to derive other parameters, including eversion (i.e., pronation and supination). In other embodiments, the markers 1002 can be positioned in different or additional locations on the runner, such as the runner's torso, hips, both of the runner's legs, and/or other suitable locations. In further embodiments, the monitoring system can perform the body motion analysis from data received from fewer than five markers, more than five markers, and/or different types of markers, including passive, visually identifiable markers and/or active sensors.

Figure 13:
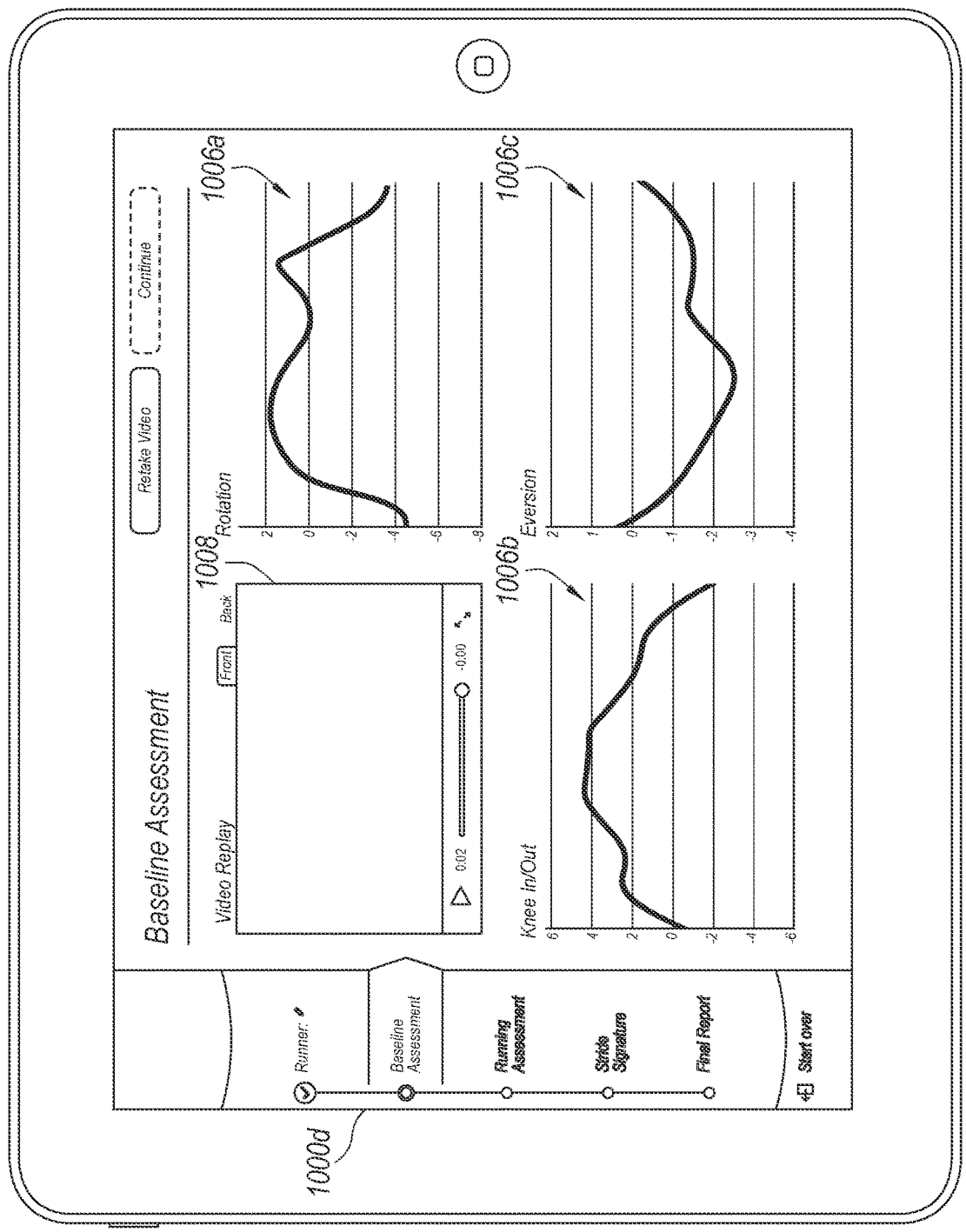

As the runner performs the unloaded state exercise, the video camera records the runner's movement from the front and the back, and in particular, the movement of the markers 1002. The body motion analysis system then uses the recorded information to analyze various parameters of the runner's body movement in the unloaded state. For example, the information from the markers 1002 can be used to determine tibia rotation, knee movement (e.g., inward and outward), eversion (i.e., pronation and supination), and/or other features of the runner's body movement. As shown in FIG. 13, the fourth block diagram 1000d includes a plurality of graphs (identified individually as first through third graphs 1006a-c, respectively; referred to collectively as "graphs 1006") that illustrate these parameters to the user. In the illustrated embodiment, the first graph 1006a includes a curve showing the runner's leg or tibia rotation in the unloaded state, the second graph 1006b includes a curve showing the runner's knee movement inward and outward in the unloaded state, and the third graph 1006c includes a curve showing the runner's eversion in the unloaded state. In other embodiments, additional or different graphs can be displayed to illustrate additional or different parameters of the runner's body movement. In addition, the fourth block diagram 1000d also includes a video inset 1008 that allows the user to play back the front and back recordings of the runner's unloaded state movement.

Figure 14:
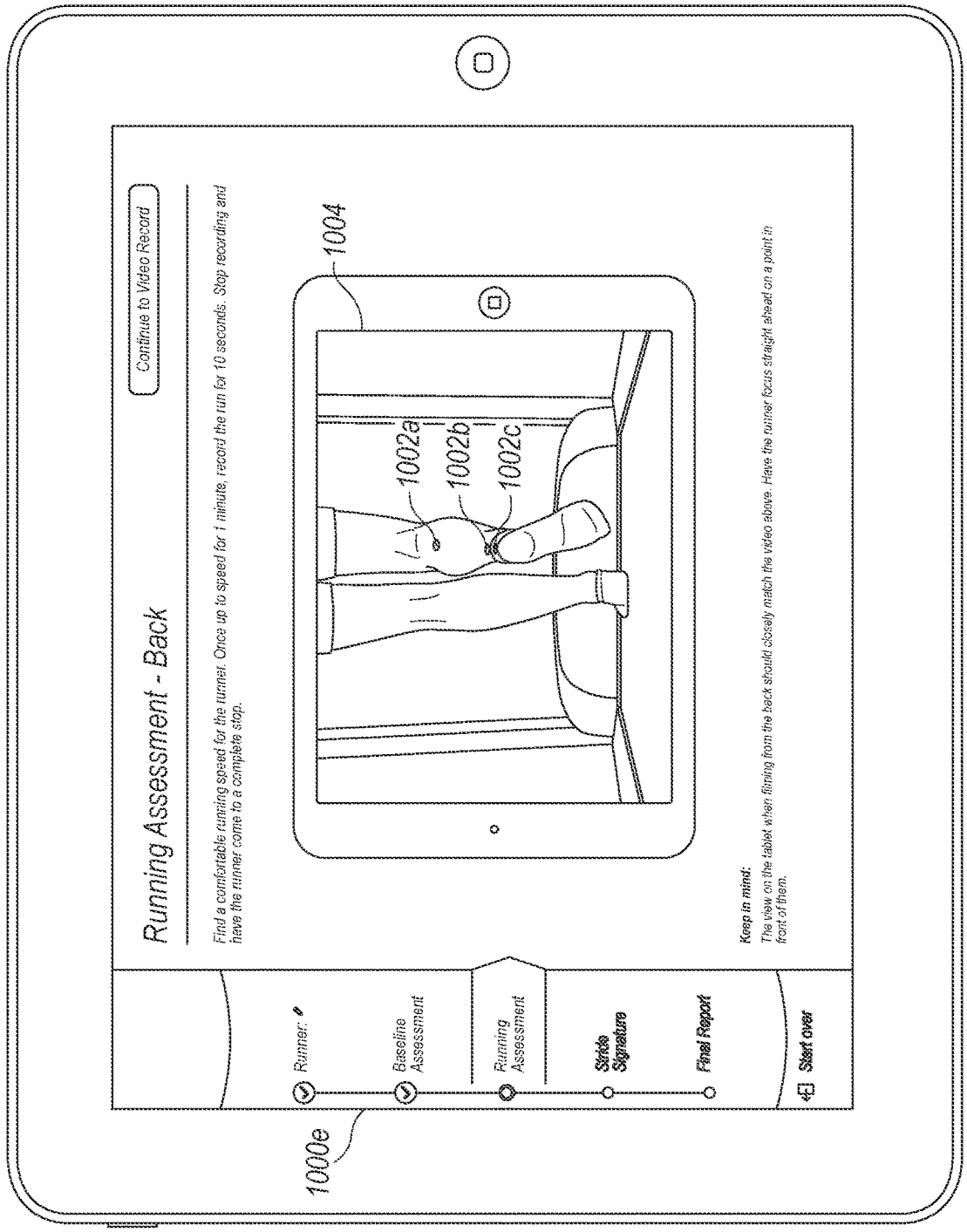
Figure 15:
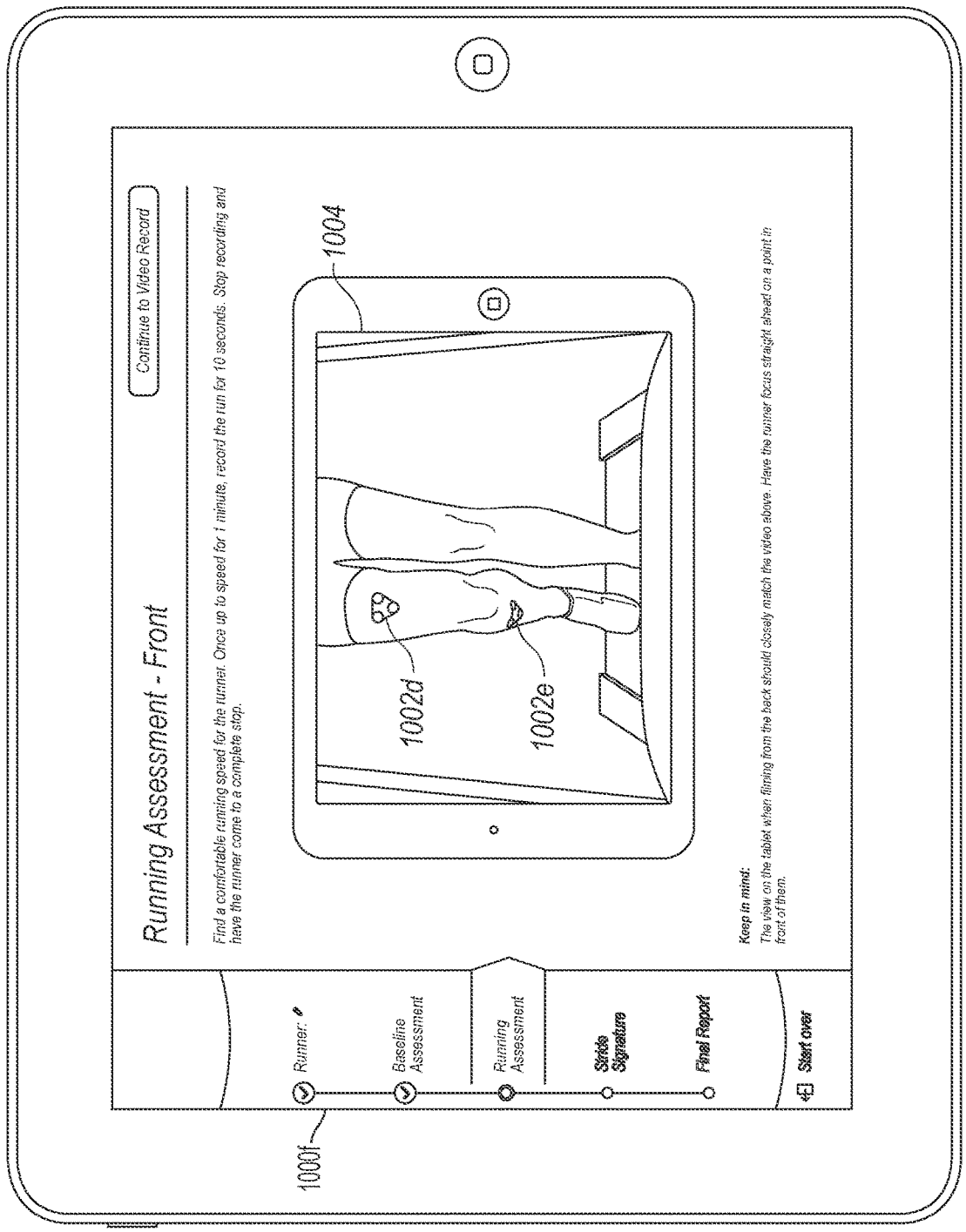

The application continues to the fifth block diagram 1000e (FIG. 14) and the sixth block diagram 1000f (FIG. 15) to perform a running assessment of the runner's body movement in a loaded state. Similar to the baseline assessment, the running assessment includes recording the runner from the back (FIG. 14) and front (FIG. 15) as the runner performs the loaded state exercise (e.g., running on a treadmill). The front and back recordings can be taken sequentially or simultaneously. As shown in FIGS. 14 and 15, the fifth and sixth block diagrams 1000e and 1000f can provide instructions for performing the running assessment, including instructions related to how long and how fast the runner should run and/or how long the video recording of the run should last. In the illustrated embodiment, for example, the block diagrams 1000e-f instruct the runner to run at a comfortable running speed for one minute, and that the recording should be approximately 10 seconds. In other embodiments, the run duration, speed, recording length, and/or exercise can differ in accordance with the information desired to perform the body motion analysis in the loaded state. As further shown in FIGS. 14 and 15, the block diagrams 1000e-f can also include a video 1004 that visually illustrates an example of the loaded state movement and/or visually indicates the desired camera view for recording the runner moving in the loaded state.

Figure 16:
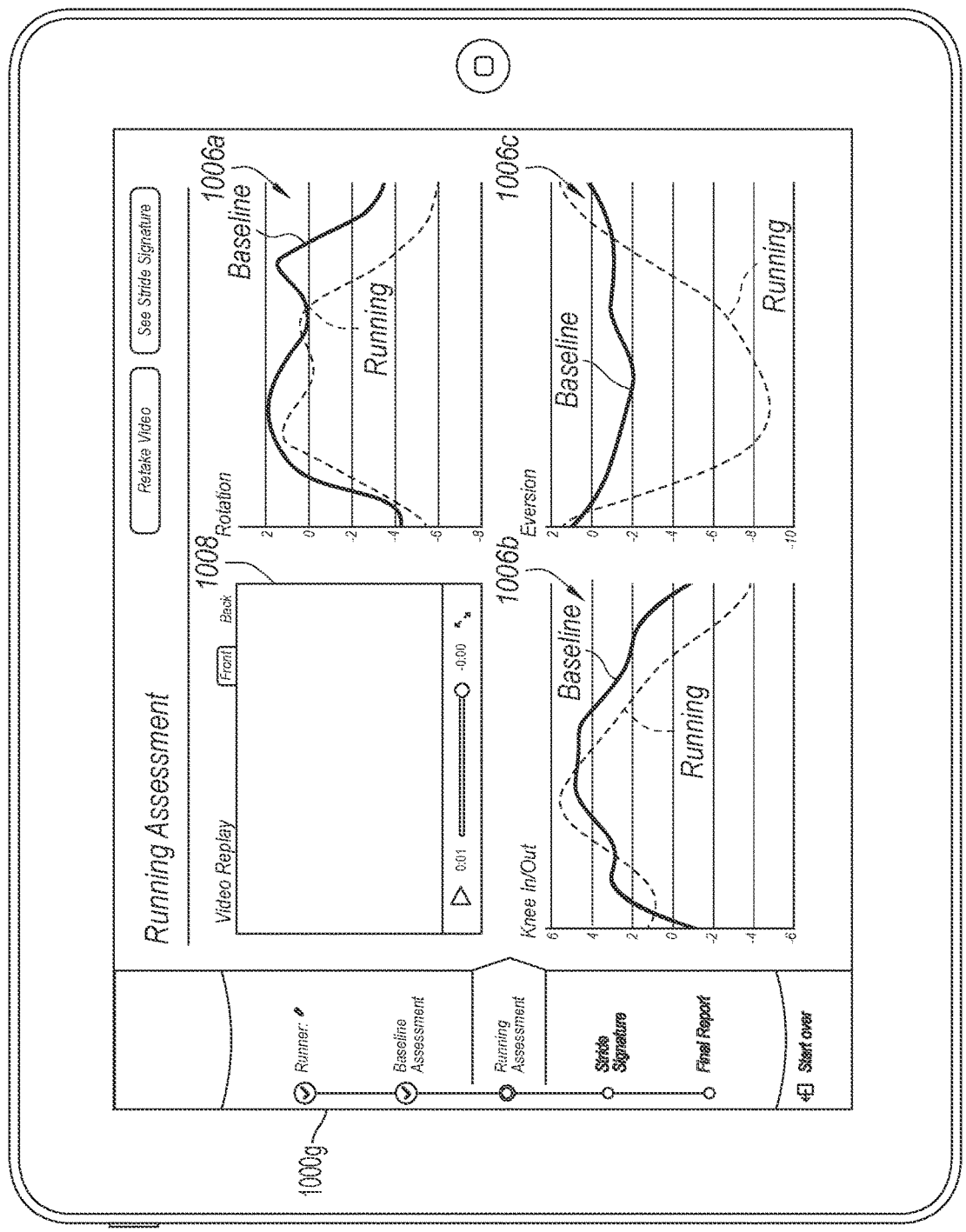
Figure 17:
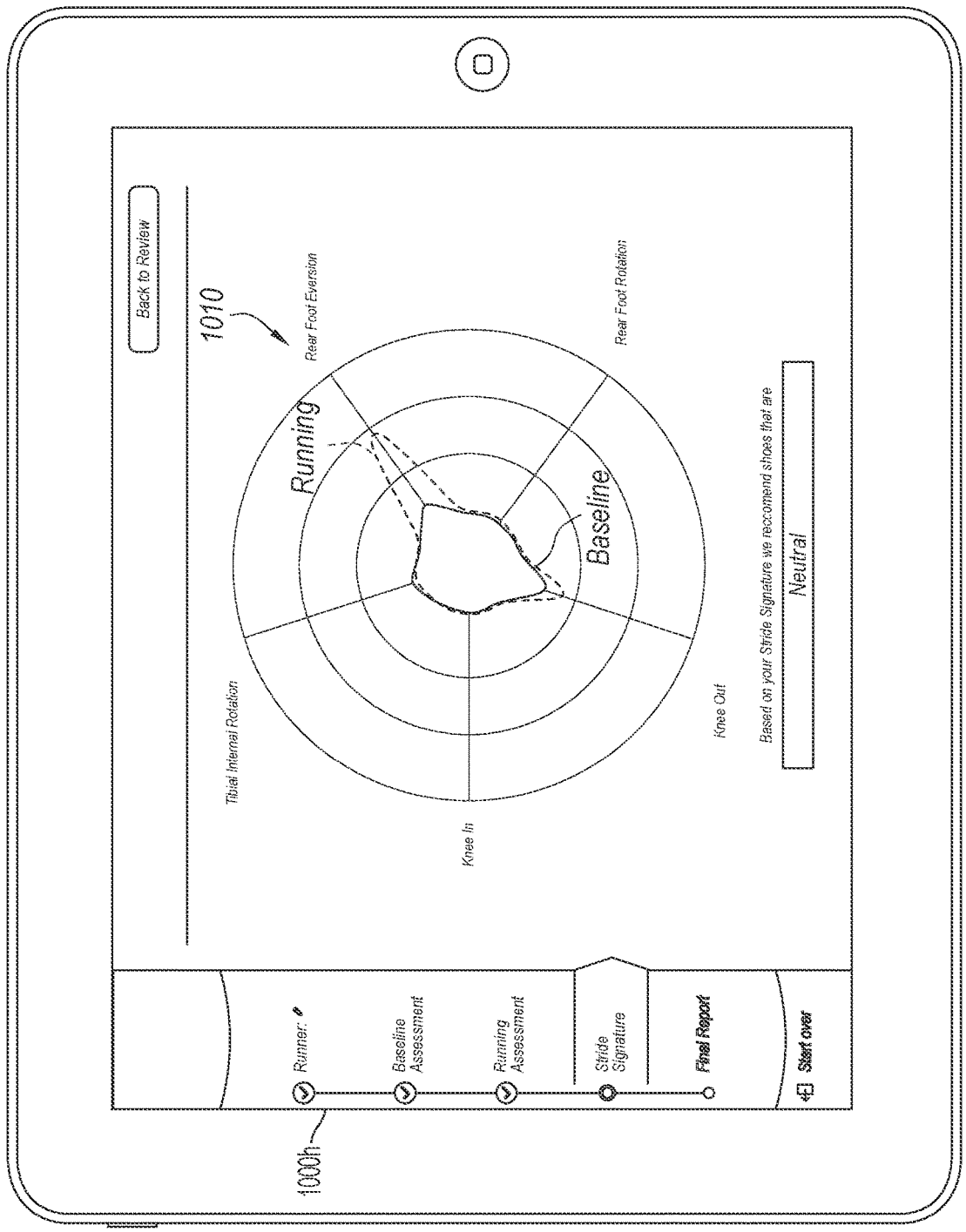

As the runner performs the loaded state exercise, the video camera records the runner's movement from the front and the back, and in particular, the movement of the markers 1002 attached to the runner. The body motion analysis system then uses the recorded information to analyze various parameters of the runner's body movement in the loaded state and display the results graphically. As shown in FIG. 16, for example, the seventh block diagram 1000g includes graphs 1006 with curves that indicate the runner's rotation, knee movement, and eversion in the loaded state, As further shown in FIG. 16, these curves can be superimposed on the curves illustrating the runner's body movement in the unloaded state to provide a visual representation of the changes in certain parameters of the runner's body movement from the unloaded to the loaded state. In addition, the seventh block diagram 1000g can also include a video inset 1008 that allows the user to play back the front and back recordings of the runner's loaded state movement.

After the unloaded state and loaded state body motion assessments are complete, the application can continue to the eighth block diagram 1000h (FIG. 17) to provide a graphical representation 1010 of the runner's baseline body motion and running or loaded state body motion. The graphical representation 1010 combines the individual parameters measured or derived during the body motion analysis to provide an overall assessment of the change in the runner's body movement between the unloaded and loaded states. For example, the graphical representation 1010 on the eighth block diagram 1000h illustrates changes in the runner's tibia internal rotation, rear foot eversion, rear foot rotation, knee movement inward, and knee movement outward.

This information is then used by the body motion system to provide the user with guidance as to what type of shoe (e.g., running shoe) the runner should use to allow the runner to run or otherwise move in manner close to the runner's natural, baseline body motion. The eighth block diagram 1000h, for example, indicates that the runner should use a neutral shoe rather than a shoe that is more supportive. In other embodiments, the application can be configured to provide the runner with additional guidance as to what type of shoe or shoe features would be best suited for the runner. For example, the application can display a specific model of shoe, specific cushioning characteristics, specific support features, and/or other aspects of shoes that may help the runner move in a manner more similar to the runner's baseline body motion.

Figure 18:
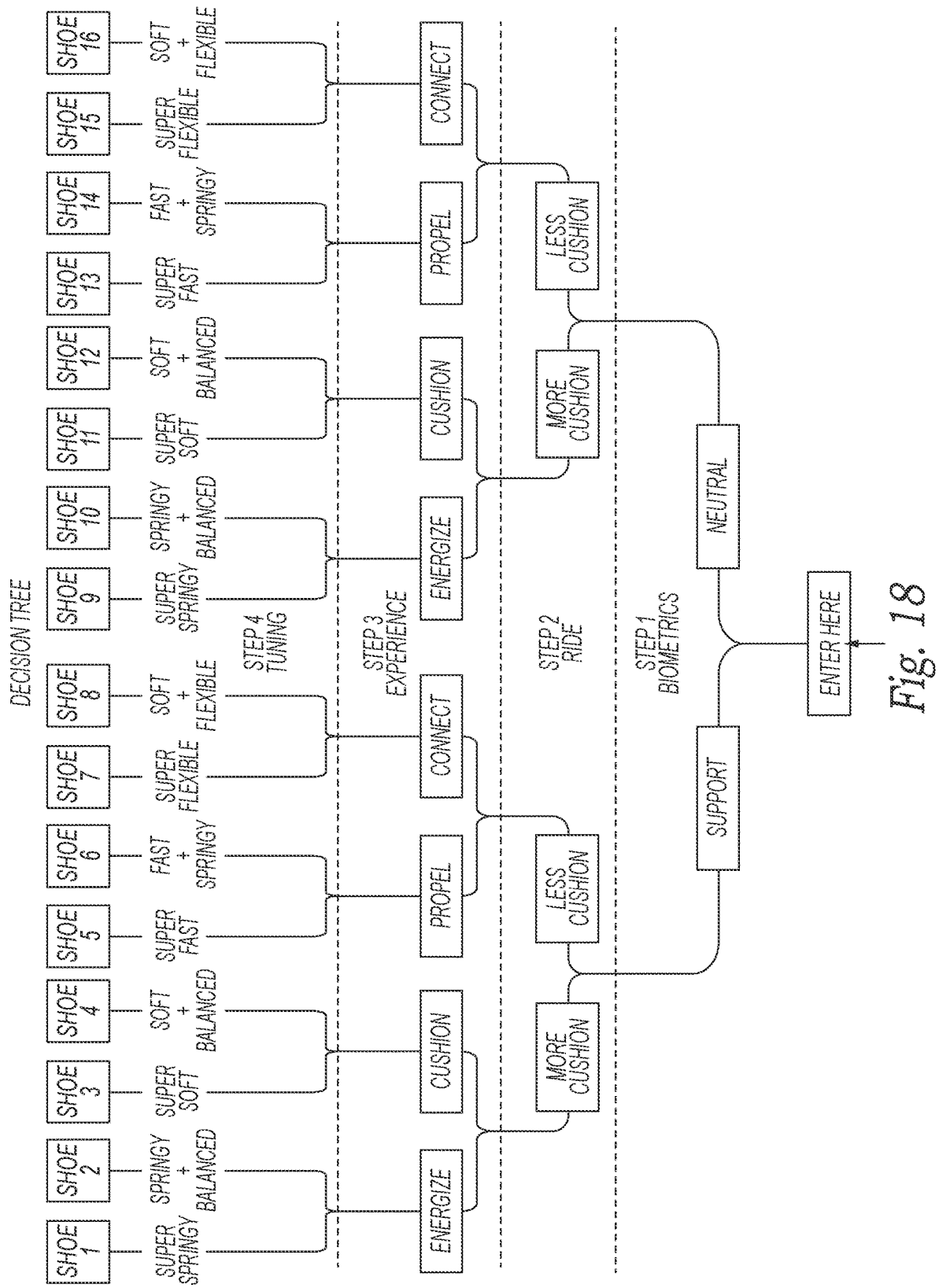
FIG. 18 is a flow chart illustrating a method of selecting a shoe based on information received from a body motion analysis performed in accordance with an embodiment of the present technology.

FIG. 18 is a flow chart 1800 illustrating a method of selecting a shoe based on the biometrics information received from the body motion analysis and the runner's preferences regarding running experience, shoe performance, and/or shoe characteristics. For example, the information provided by the application and body motion analysis systems described above can be used in conjunction with the flow chart 1800 to select shoe features on the flow chart 1800. As shown in FIG. 18, the flow chart 1800 can begin by identifying whether the runner requires a shoe with more support or a more neutral shoe based on the runner's biomechanics and the identified trend related to the runner's body motion in the unloaded and loaded states. For example, a more supportive shoe may be recommended for a runner that significantly increases internal tibia rotation and inward knee rotation when in the loaded state, whereas a neutral shoe would be recommended for a runner with different characteristics (e.g., the runner shown in FIGS. 10-17) dddddd.

As shown in FIG. 18, the flow chart 1800 provides a ride preference level with selection options based upon whether the runner would prefer a shoe with more cushioning or less cushioning. If a higher level of cushioning is selected, the flow chart 1800 progresses and provides a run-experience level with options based upon whether the runner would prefer a shoe configured to "energize" the runner's stride (e.g., include more reactive shoe performance) or provide more "cushion" (e.g., softer, less reactive shoe performance). When the selected shoe characteristic corresponds to "energize", the flow chart 1800 progresses and provides shoe-tuning level with options based upon a runner's performance feel characteristics, such as whether the shoe should provide features that are highly "springy" or provide a combination of spring and balance. When the selected shoe characteristic at the runner-experience level corresponds to "cushion", the flow chart 1800 identifies the selection options at the shoe-tuning level of whether the shoe should provide features that make the shoe soft or provide a combination of softness and balance. Based on these sequential selections at the various levels regarding the shoe characteristics and performance preferences, the flow chart 1800 identifies which shoe or shoes are recommended for the runner.

Alternatively, when less cushioning is selected at the ride preference level, the flow chart moves to the run-experience level and provides different run experience level options based upon whether the runner would prefer a shoe with features that "propel" the runner (e.g., include more reactive shoe features) or "connect" the runner closer to the running surface (e.g., less reactive shoe features and/or more direct feel to the running surface). When the selected shoe characteristic corresponds to "propel", the flow chart 1800 provides shoe tuning selection options based on the runner performance characteristics, such as whether the shoe should provide features that make the shoe fast (e.g., decreased shoe weight) or provide features that make the shoe both springy and fast. When the selected shoe characteristic corresponds to "connect", the flow chart continues 1800 identifies the selection options of whether the shoe should provide features that make the shoe highly flexibly or provide features that make the shoe both flexible and soft. Based on these sequential selections, the flow chart 1800 identifies which shoe or shoes are recommended for the runner. In the illustrated embodiment, the flow chart 1800 provides similar selection options at similar selection levels if the biometric information identifies that the runner should use a more neutral shoe. In other embodiments, additional or different shoe features and/or selection levels can be included in the flow chart 1800 and/or some of the categories of shoe features may be omitted.

In various embodiments, the body motion analysis systems described above can be used to guide a runner through the flow chart 1800. For example, the body motion analysis may make a determination on whether the runner should wear a neutral shoe or a more supportive shoe. The runner can then use this information to make the initial decision of "neutral" or "support" in the flow chart 1800, and then continue through the flow chart 1800 based on person preference and shoe requirements until the flow chart 1800 ends and recommends one or more specific shoes. In other embodiments, body motion analysis systems may provide more detailed recommendations, such as the level of cushioning and/or type of shoe experience, to further guide the runner through the flow chart 1800. In further embodiments, the flow chart 1800 may be part of an algorithm used by the body motion analysis system or associated application to fully automate selecting specific shoe features and provide specific shoe recommendations.

CONCLUSION

From the foregoing, it will be appreciated that specific embodiments of the technology have been described herein for purposes of illustration, but that various modifications may be made without deviating from the spirit and scope of the technology. Further, while various advantages associated with certain embodiments of the disclosure have been described above in the context of those embodiments, other embodiments may also exhibit such advantages, and not all embodiments need necessarily exhibit such advantages to fall within the scope of the disclosure.

We claim:

1. A method performed by a computing device for evaluating lower body movement and recommending footwear, the method comprising:

receiving from one or more motion detection devices first body movement data related to first movements associated with lower body portions of a human in a first state related to first loads applied to the human's body;

storing the first body movement data in a memory coupled to a controller;

receiving from the one or more motion detection devices second body movement data related to second movements associated with the lower body portions of a human in a second state related to second loads applied to the human's body, wherein the second loads are greater than the first loads;

storing the second body movement data in the memory;

comparing with the controller the second body movement data to the first body movement data;

based on the comparison, identifying a trend corresponding to a change in the movement of the lower body portions from the first state to the second state;
analyzing the trend and characteristics of a plurality of footwear models, and
recommending footwear for the human based on the analysis of the trend, wherein the footwear is configured to counteract trends of movement of the lower body portions away from the first state.

2. The method of claim 1, further comprising displaying on a display the footwear recommendation.

3. The method of claim 1 wherein the one or more motion detection devices comprise a plurality of sensors coupled to the controller.

4. The method of claim 1 wherein the one or more motion detection devices comprise a plurality of markers configured to be coupled to portions of the human body.

5. The method of claim 1 wherein the one or more motion detection devices comprises an accelerometer configured to be worn or carried by the human body.

6. The method of claim 1 wherein one or more motion detection devices comprises one or more video cameras configured to capture video images of the first and second movements.

7. The method of claim 6 wherein the one or more video cameras are configured to capture images of movement of the lower body portions from the first state to the second state.

8. The method of claim 1, further comprising correlating the first and second movements to inward and outward knee movement of the human in the first and second states, and to tibia rotation in the first and second states.

9. The method of claim 1 wherein receiving the first and second body movement data comprises receiving data related to inward and outward knee movement of the human in the first state and the second state, and data related to tibia rotation of the human in the first state and the second state.

10. The method of claim 1 wherein receiving the first body movement data comprises receiving data related to lower body movement while the lower body portions are in a neutral state.

11. The method of claim 1 wherein receiving second body movement data comprises receiving data related to lower body movement while the human runs for a period of time.

12. The method of claim 11 wherein the second state is a first loaded state and the trend is a first trend, and wherein receiving second body movement data comprises receiving data related to lower body movement while the human is in the second state for a first period of time, and the method further comprises:
receiving from the one or more motion detection devices third body movement data related while the human is in a second loaded state for a second period of time greater than the first period of time;
storing in the memory the third body movement data;
comparing with the controller the third body movement data to the first body movement data;
based on the comparison of the first and third body movements data, identifying a second trend corresponding to a change in the movement of the lower body portions from the first state to the second unloaded state;
analyzing the second trend related to characteristics of the plurality of footwear models, and
recommending a footwear for the human based on the analysis of the second trend, wherein the footwear is configured to counteract movement of the lower body portions away from the first state.

13. The method of claim 1 wherein the first state is an unloaded state and the second state is a first loaded state and the trend is a first trend, and wherein the method further comprises:
receiving data related to lower body movement of the human in a second loaded state, wherein the second loaded state differs from the first loaded state;
characterizing the lower body movement of the human in the second loaded state;
identifying a second trend corresponding to a change in the lower body movement from the unloaded state to the second loaded state; and
modifying the footwear recommendations in response to changes from the first trend to the second trend.

14. The method of claim 1, further comprising:
receiving data related to lower body movement of the human during a series of running exercises over a period of time;
identifying changes in the trend; and
modifying the footwear recommendations in response to changes in the trend.

15. A method for evaluating lower body movement, the method comprising:
receiving first data related to lower body movement of a human in a first state related to first loads applied to the human's body and based on the human moving in the first state;
storing the first recorded data in a memory coupled to a controller;
defining a baseline based on the lower body movement of the human in the first state;
receiving second data related to lower body movement of the human in a second state related to second loads applied to the human's body, wherein the second loads are greater than the first loads based on movement data relating to the human moving in the loaded state;
storing the second recorded data in the memory;
determining a trend in lower body movement from the baseline to the lower body movement in the second state;
analyzing with the controller the trend related to characteristics of a plurality of footwear models; and
recommending footwear that counteracts trends away from the baseline.

16. The method of claim 15 wherein receiving data related to lower body movement of the human in the first state and the second state comprises:
receiving data related to inward and outward knee motion of the human; and
receiving data related to lower leg rotation of the human.

17. The method of claim 15 wherein receiving data related to lower body movement of the human in the first state and the second state comprises receiving data related to linear and angular ranges of motion of a knee and a leg of the human.

18. The method of claim 15, further comprising:
positioning at least two markers on a backside of a leg of the human; and
positioning at least two markers on a front side of the leg of the human,
wherein receiving the data comprises recording movement of the markers as the human moves in the first and second states.

19. The method of claim 15 wherein the first state is an unloaded state and the second state is a first loaded state and the trend is a first trend, and wherein the method further comprises:

receiving third recorded data related to lower body movement of the human in a second loaded state, wherein the second loaded state differs from the first loaded state;

characterizing the lower body movement of the human in the second loaded state;

identifying a second trend corresponding to a change in the lower body movement from the unloaded state to the second loaded state; and modifying the footwear recommendations in response to changes from the first trend to the second trend.

20. A system for recommending footwear, the system comprising:

one or more motion detection devices configured for use in detection of movement of human body in first and second states;

a data recording device configured to record, via the one or more motion detection devices, lower body movement of the human in the first and second states, wherein the first state is related to first loads applied to the human's body and based on the human moving in the first state and wherein the second state is related to second loads applied to the human's body, wherein the second loads are greater than the first loads;

a memory;

a controller communicatively coupled to one or more motion detection devices, wherein the controller is configured to, using one or more processors:

receive data from the one or more motion detection devices, wherein the data relates to lower body movement of the human in the first state and the second state;

characterize the lower body movement of the human in the first state and the second state;

determine a trend corresponding to a change in the lower body movement from the first state to the second state; and recommending footwear based on the trend, wherein the footwear is configured to counteract trends away from the lower body movement in the first state.

21. The system of claim 20 wherein the one or more motion detection devices comprises a video camera configured to capture images of the lower body movement of the human in the first and second states.

22. The system of claim 20 wherein the one or more motion detection devices comprises an accelerometer configured to be worn or carried by the human body.

23. The system of claim 20 wherein the one or more motion detection devices comprises a plurality of sensors or markers configured to be coupled to the human body.

24. The system of claim 20 wherein the first state corresponds to a neutral state and the second state corresponds to a loaded state.

* * * * *